US010380404B2

(12) United States Patent
Kim et al.

(10) Patent No.: US 10,380,404 B2
(45) Date of Patent: Aug. 13, 2019

(54) METHOD AND APPARATUS TO DETECT THREE-DIMENSIONAL PATTERN INFORMATION OF A TOUCH OBJECT

(71) Applicant: Samsung Display Co., Ltd., Yongin-si (KR)

(72) Inventors: Young Chan Kim, Yongin-si (KR); Il Nam Kim, Yongin-si (KR); Kyung Tea Park, Yongin-si (KR); Byung Han Yoo, Yongin-si (KR); Tae Hee Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 15/682,077

(22) Filed: Aug. 21, 2017

(65) Prior Publication Data

US 2018/0060641 A1 Mar. 1, 2018

(30) Foreign Application Priority Data

Aug. 23, 2016 (KR) .......................... 10-2016-0107014

(51) Int. Cl.
*G06K 9/00* (2006.01)
*A61B 5/1172* (2016.01)

(52) U.S. Cl.
CPC ....... *G06K 9/00046* (2013.01); *G06K 9/0004* (2013.01); *G06K 9/00013* (2013.01); *G06K 9/00026* (2013.01); *G06K 9/00033* (2013.01); *A61B 5/1172* (2013.01)

(58) Field of Classification Search
CPC ............ G06K 9/00013; G06K 9/0004; G06K 9/0008; G02F 1/13338; A61B 5/1172
See application file for complete search history.

(56) References Cited

U.S. PATENT DOCUMENTS

| 4,151,512 A | * | 4/1979 | Riganati | G06F 21/32 382/125 |
| 7,403,271 B2 | | 7/2008 | Kim et al. | |
| 8,933,894 B2 | * | 1/2015 | Park | G06F 3/0412 345/173 |
| 2015/0187837 A1 | * | 7/2015 | Zhao | H01L 27/14812 257/40 |
| 2016/0343770 A1 | * | 11/2016 | Fan | H01L 27/14643 |
| 2017/0109561 A1 | * | 4/2017 | Wyrwas | G06K 9/00046 |
| 2017/0270339 A1 | * | 9/2017 | Zou | G06K 9/0004 |
| 2017/0300736 A1 | * | 10/2017 | Song | G06K 9/00033 |
| 2017/0315293 A1 | * | 11/2017 | Bang | G02B 6/102 |

FOREIGN PATENT DOCUMENTS

| KR | 10-0575144 | 4/2006 |
| KR | 10-1493333 | 2/2015 |

* cited by examiner

*Primary Examiner* — Maurice C Smith
(74) *Attorney, Agent, or Firm* — H.C. Park & Associates, PLC

(57) ABSTRACT

A display device includes a substrate, display elements, a window, and a photo sensor array. The substrate includes a display area and a non-display area. The display elements overlap the display area. The window is disposed on the substrate. The photo sensor array is disposed between the substrate and the window. The photo sensor array is configured to sense three-dimensional pattern information (e.g., epidermal ridge information) of a user via light reflected from a touch input of the user. One or more of the display elements is configured to illuminate a contact area of the touch input with the light.

12 Claims, 14 Drawing Sheets

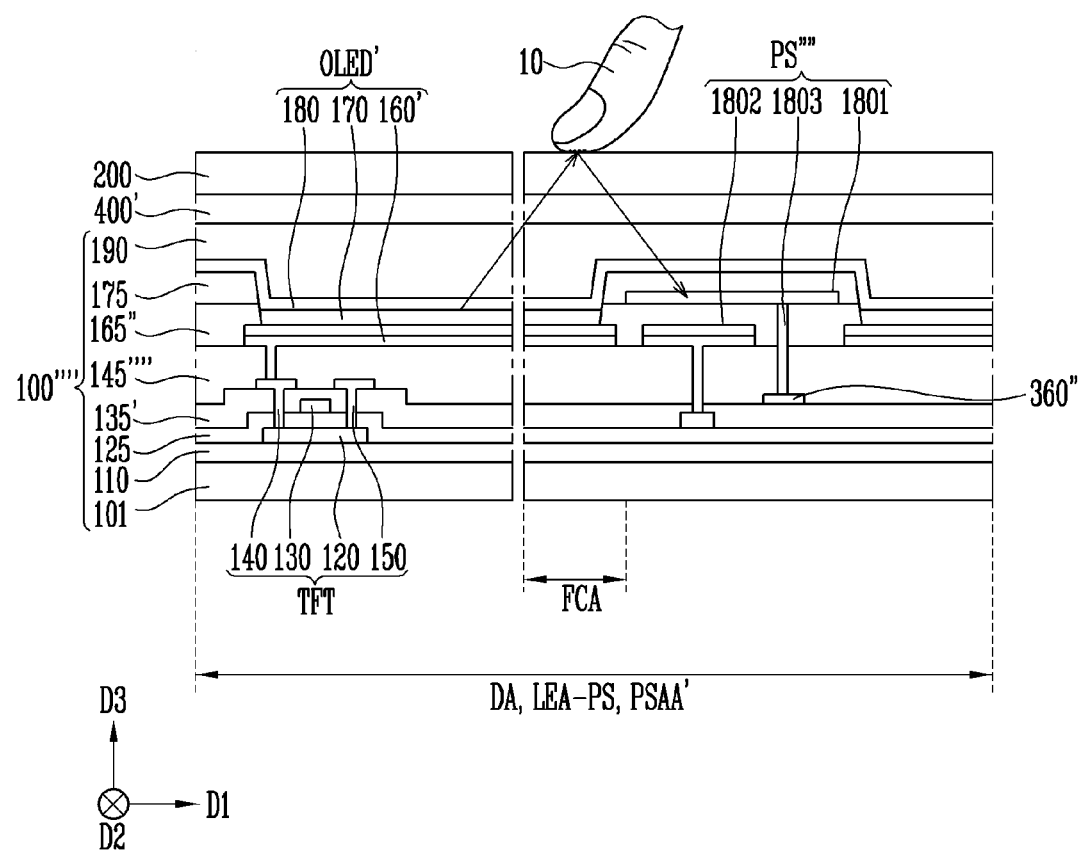

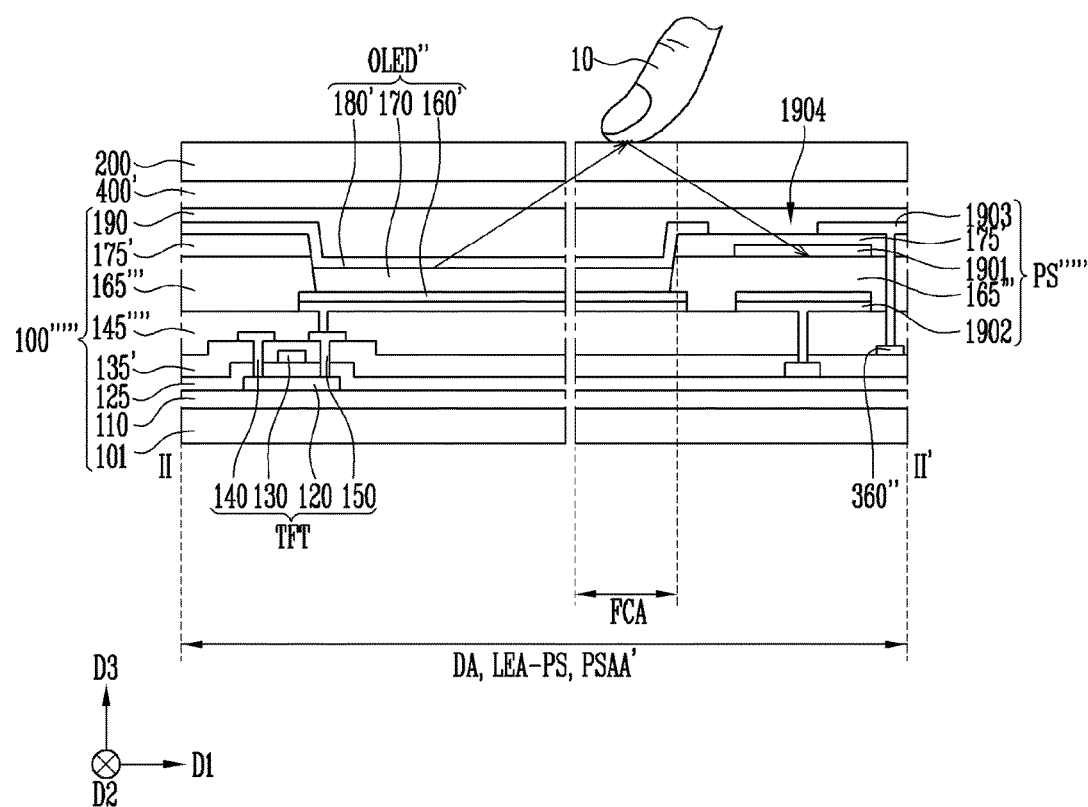

METHOD AND APPARATUS TO DETECT THREE-DIMENSIONAL PATTERN INFORMATION OF A TOUCH OBJECT

CROSS-REFERENCE TO RELATED APPLICATION

This application claims priority from and the benefit of Korean Patent Application No. 10-2016-0107014, filed on Aug. 23, 2016, which is hereby incorporated by reference for all purposes as if fully set forth herein.

BACKGROUND

Field

One or more exemplary embodiments relate to detection of three-dimensional pattern information, and, more particularly, to display technology to detect three-dimensional pattern information of a touch object.

Discussion

In addition to a function of displaying an image, various functions may be added to display devices. For instance, fingerprint sensing elements (or components) and an associated fingerprint sensing function may be added to a display device. For instance, a display device having a fingerprint sensing element may sense fingerprint information using an optical sensing technique or a capacitive sensing technique. The optical sensing technique may, for example, sense a fingerprint by detecting a difference in reflected light that varies depending on whether the reflected light is reflected from a ridge or a valley of the fingerprint. The capacitive sensing technique may, for instance, sense a fingerprint by detecting a difference in capacitance that varies depending on the ridges and valleys of the fingerprint. Typically, a fingerprint sensing element is assembled as a component of the display device. As the size of display devices decrease, spatial limitations may hinder the addition of such external fingerprint sensors.

The above information disclosed in this section is only for enhancement of an understanding of the background of the inventive concepts, and, therefore, it may contain information that does not form prior art already known to a person of ordinary skill in the art.

SUMMARY

One or more exemplary embodiments provide a display device to sense three-dimensional pattern information of a touch object, such as epidermal ridge information of an appendage, e.g., fingerprint information of a human finger.

One or more exemplary embodiments provide a display panel to detect three-dimensional pattern information of a touch object.

One or more exemplary embodiments provide an apparatus to generate information corresponding to a three-dimensional pattern of a touch object.

Additional aspects will be set forth in the detailed description which follows, and, in part, will be apparent from the disclosure, or may be learned by practice of the inventive concepts.

According to one or more exemplary embodiments, a display device includes a substrate, display elements, a window, and a photo sensor array. The substrate includes a display area and a non-display area. The display elements overlap the display area. The window is disposed on the substrate. The photo sensor array is disposed between the substrate and the window. The photo sensor array is configured to sense epidermal ridge information of a user via light reflected from a touch input of the user. One or more of the display elements is configured to illuminate a contact area of the touch input with the light.

According to one or more exemplary embodiments, a display panel includes a display area and a non-display area. The display area includes pixels to illuminate a window with light. The non-display area includes a photosensitive detector to detect at least some of the light reflected from a three-dimensional pattern on a portion of the window. The portion of the window overlaps the display area. The photosensitive detector is communicatively coupled to at least one processor to generate information corresponding to the three-dimensional pattern.

According to one or more exemplary embodiments, an apparatus includes at least one processor and at least one memory. The least one memory includes one or more sequences of one or more instructions that, in response to being executed by the at least one processor, cause the apparatus at least to: control pixels of a display panel to display an image via first illumination; control, in response to detection of a first interaction of an object with a surface of the display panel, at least some of the pixels to illuminate a portion of the object with second illumination, the second illumination being different from the first illumination; control one or more photo sensors of the display panel to sense third illumination, the third illumination corresponding to at least some of the second illumination reflected from the object; and generate, in accordance with the third illumination, information corresponding to a three-dimensional pattern of the portion of the object.

According to one or more exemplary embodiments, a display panel includes a patterned layer, an electroluminescent layer, a photosensitive layer, and an encapsulation layer. The patterned layer includes a pattern of openings in a display area. The electroluminescent layer is disposed in a portion of an opening among the openings. The photosensitive layer is disposed on the patterned layer between a pair of openings among the openings. The photosensitive layer is configured to detect light reflected from a three-dimensional pattern overlapping a portion of the display area. The encapsulation layer overlaps the patterned layer.

According to one or more exemplary embodiments, a three-dimensional pattern sensor may form a portion of a display. In this manner, spatial limitations associated with the incorporation of modular sensors in a conventional display may be reduced. Further, one or more exemplary embodiments improve detection sensitivity of a three-dimensional pattern sensor by at least improving light receiving efficiency of the three-dimensional pattern sensor.

The foregoing general description and the following detailed description are exemplary and explanatory and are intended to provide further explanation of the claimed subject matter.

BRIEF DESCRIPTION OF THE DRAWINGS

The accompanying drawings, which are included to provide a further understanding of the inventive concepts, and are incorporated in and constitute a part of this specification, illustrate exemplary embodiments of the inventive concepts, and, together with the description, serve to explain principles of the inventive concepts.

FIG. 18 is a cross-sectional view of a display device, according to one or more exemplary embodiments.

FIG. 19 is a cross-sectional view of a display device taken along sectional line II-II' of FIG. 15, according to one or more exemplary embodiments.

DETAILED DESCRIPTION OF THE ILLUSTRATED EMBODIMENTS

Figure 1:
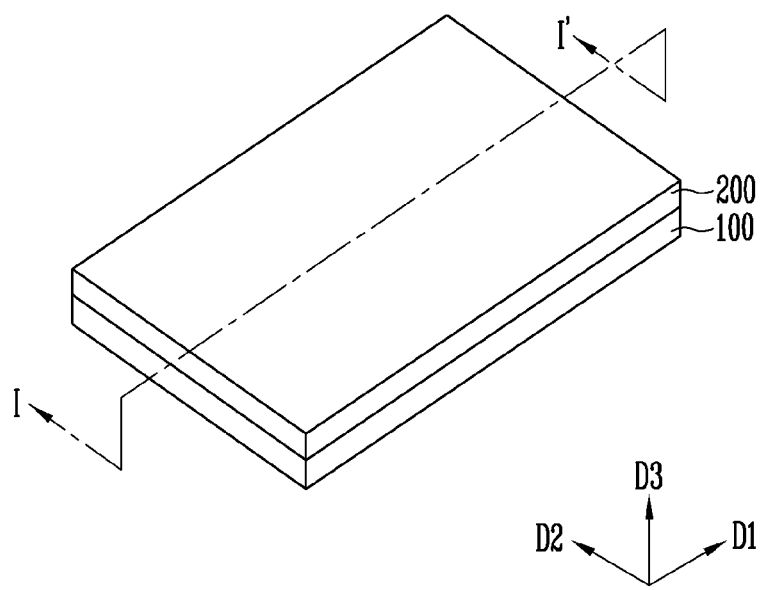
FIG. 1 is a perspective view of a display device, according to one or more exemplary embodiments.

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments.

As customary in the field, exemplary embodiments are described and illustrated in the drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of exemplary embodiments may be physically separated into two or more interacting and discrete blocks, units, and/or modules without departing from the spirit and scope of the inventive concepts. Further, the blocks, units, and/or modules of exemplary embodiments may be physically combined into more complex blocks, units, and/or modules without departing from the spirit and scope of the inventive concepts.

Unless otherwise specified, the illustrated exemplary embodiments are to be understood as providing exemplary features of varying detail of various exemplary embodiments. Therefore, unless otherwise specified, the features, components, modules, layers, films, panels, regions, and/or aspects of the various illustrations may be otherwise combined, separated, interchanged, and/or rearranged without departing from the disclosed exemplary embodiments. Further, in the accompanying figures, the size and relative sizes of layers, films, panels, regions, etc., may be exaggerated for clarity and descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element or layer is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. Further, the D1-axis, the D2-axis, and the D3-axis are not limited to three axes of a rectangular coordinate system, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various elements, components, regions, layers, and/or sections, these elements, components, regions, layers, and/or sections should not be limited by these terms. These terms are used to distinguish one element, component, region, layer, and/or section from another element, component, region, layer, and/or section. Thus, a first element, component, region, layer, and/or section discussed below could be termed a second element, component, region, layer, and/or section without departing from the teachings of the present disclosure.

Spatially relative terms, such as "beneath," "below," "lower," "above," "upper," and the like, may be used herein for descriptive purposes, and, thereby, to describe one element or feature's relationship to another element(s) or feature(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Various exemplary embodiments are described herein with reference to sectional illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not be construed as limited to the particular illustrated shapes of regions, but are to include deviations in shapes that result from, for instance, manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. In this manner, regions illustrated in the drawings are schematic in nature and shapes of these regions may not illustrate the actual shapes of regions of a device, and, as such, are not intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

Figure 2:
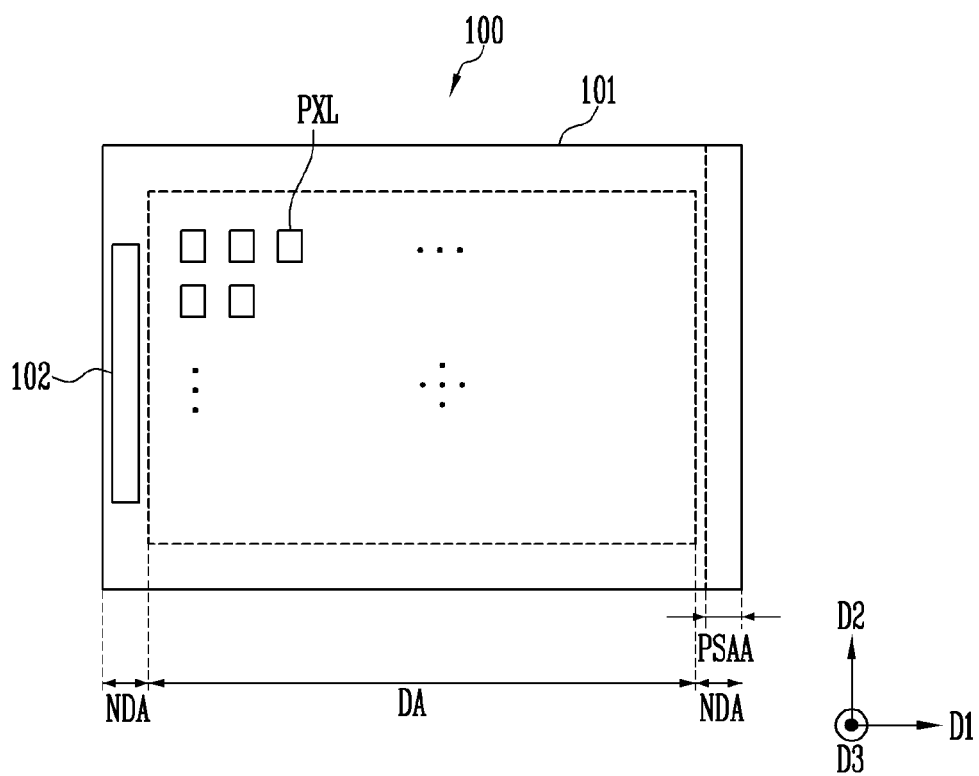
FIG. 2 is a plan view of a display panel of the display device of FIG. 1, according to one or more exemplary embodiments.
Figure 3:
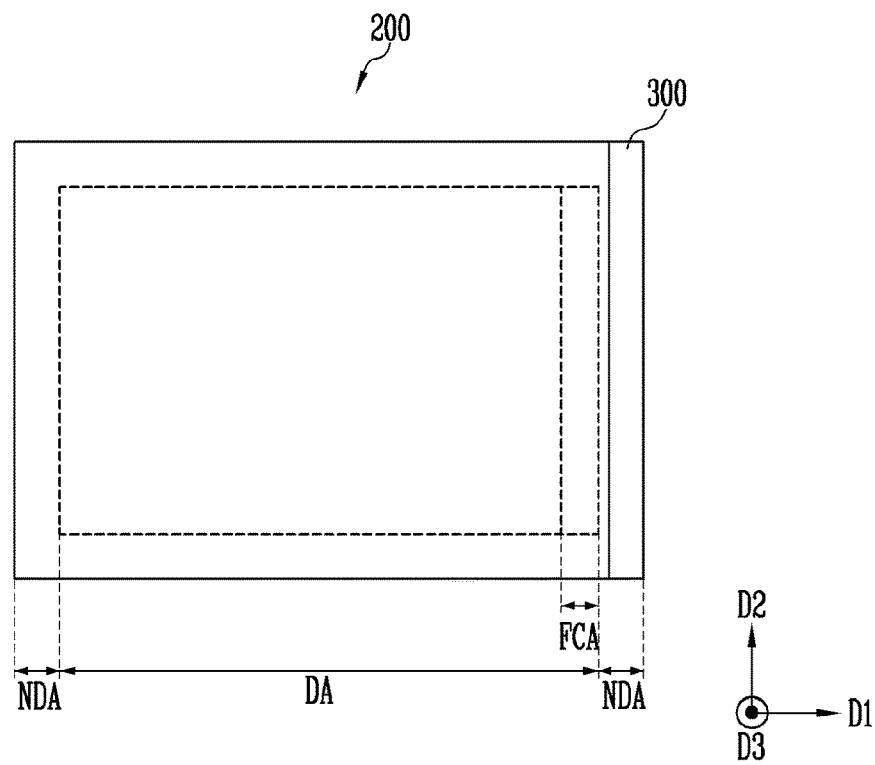
FIG. 3 is a plan view of a window of the display device of FIG. 1, according to one or more exemplary embodiments.
Figure 4:
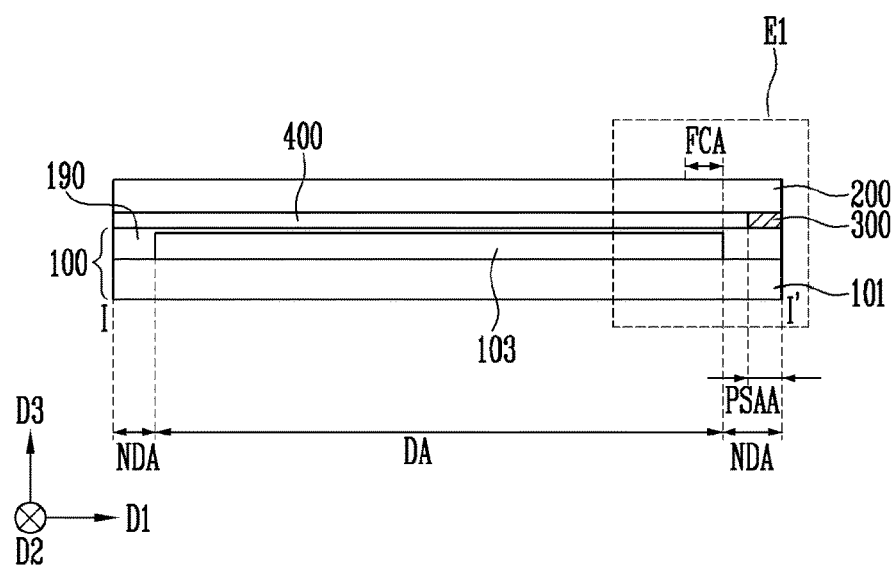
FIG. 4 is a cross-sectional view of the display device of FIG. 1 taken along sectional line I-I', according to one or more exemplary embodiments.

FIG. 1 is a perspective view of a display device, according to one or more exemplary embodiments. FIG. 2 is a plan view of a display panel of the display device of FIG. 1, according to one or more exemplary embodiments. FIG. 3 is a plan view of a window of the display device of FIG. 1, according to one or more exemplary embodiments. FIG. 4 is a cross-sectional view of the display device of FIG. 1 taken along sectional line I-I', according to one or more exemplary embodiments.

Referring to FIGS. 1 to 4, the display device may be provided in various shapes and configurations. For example, the display device may be provided in a rectangular plate shape having two pairs of parallel sides. When the display device is provided with the rectangular plate shape, any pair of sides out of the two pairs of sides may be longer than the other pair of sides. For convenience, the display device will be described and illustrated with a rectangular plate shape having a pair of long sides and a pair of short sides. The extending direction of the long sides is in a first direction D1, the extending direction of the short sides is in a second direction D2, and a thickness of the display device is in a third direction D3.

According to one or more exemplary embodiments, the display device includes a display panel 100 in which display elements (or components) 103 for displaying an image are provided and a window 200 provided on a surface (e.g., an upper surface) of the display panel 100. The display device may include an electronic device (or structure) that recognizes a touch event of an object, such as an appendage (e.g., a finger, a palm, a foot, etc.) of a user, a separate input means (e.g., stylus, pen, informational tag, etc.) and/or the like, with a surface of the display device, such as a surface of the window 200. The object may include a three-dimensional pattern, such as a pattern of epidermal ridges (e.g., fingerprint, palm print, foot print, etc.) of an appendage of the user, a three-dimensional bar code of an informational tag, and/or the like. In this manner, the electronic device may also sense the three-dimensional pattern, which may correspond to a fingerprint of the user, the three-dimensional bar code, etc.

The display panel 100 includes a base substrate 101 and the display elements 103 provided on the base substrate 101. The base substrate 101 may include a display area DA in which an image is displayed and a non-display area NDA disposed outside the display area DA. For instance, the non-display area NDA may surround at least one edge of the display area DA.

The display area DA of the base substrate 101 is an area in which the display elements 103 including a plurality of pixels PXL are provided to display an image. The image may include arbitrary visual information, e.g., text, videos, pictures, two-dimensional or three-dimensional images, and the like. For instance, the plurality of pixels PXL may be located in the area defined by a plurality of data lines (not shown) and a plurality of scan lines (not shown). The plurality of data lines may be arranged along the second direction D2, and the plurality of scan lines may be arranged along the first direction D1. Also, the plurality of scan lines may provide scan signals to the plurality of pixels PXL so that the plurality of pixels PXL may be turned on according to the scan signals. The scan signals may be provided to the plurality of pixels PXL sequentially, thereby the plurality of pixels PXL may be driven sequentially. In one or more exemplary embodiments, the display area DA is located at a central portion of the display panel 100, and may have a relatively large area compared to the non-display area NDA.

The base substrate 101 may be made of an insulative material having flexibility; however, exemplary embodiments are not limited thereto or thereby. The base substrate 101 may be made of various materials, e.g., glass, polymer, metal, and the like. For example, the base substrate 101 may be an insulative substrate made of an organic polymer material. The material of the insulative substrate, including the organic polymer material may include polystyrene, polyvinyl alcohol, polymethyl methacrylate, polyethersulfone, polyacrylate, polyetherimide, polyethylene naphthalate, polyethylene terephthalate, polyphenylene sulfide, polyarylate, polyimide, polycarbonate, triacetate cellulose, cellulose acetate propionate, and the like. However, the material constituting the base substrate 101 is not limited thereto or thereby. For example, the base substrate 101 may be made of fiber glass reinforced plastic (FRP).

Each of the plurality of pixels PXL may be an electroluminescent component, such as an organic light emitting element including an organic layer; however, exemplary embodiments are not limited thereto or thereby. For example, the plurality of pixels PXL may be implemented in various forms including a liquid crystal element, an electrophoretic element, an electrowetting element, and the like. The plurality of pixels PXL are provided in the display area DA of the base substrate 101, and each pixel PXL may be provided in plural numbers (e.g., may include sub-pixels) as a minimum unit for displaying an image. The pixel PXL may include an organic light emitting element that emits white light and/or colored light. The pixel PXL may emit light of any one color among red, green, blue, and white; however, exemplary embodiments are not limited thereto or thereby. For instance, a pixel PXL may emit light of a color, such as cyan, magenta, yellow, etc. The pixel PXL may include a thin film transistor (not shown) connected to a line, such as the data line, the scan line (not shown), etc., and an organic light emitting element (not shown) connected to the thin film transistor (not shown).

The non-display area NDA of the base substrate 101 is an area in which the pixels PXL are not provided, and may be a bezel area in which an image is not displayed. The bezel area may be coupled to an external case (not shown). A driving unit (not illustrated, such as a data driver or scan driver, for driving the pixels PXL may be provided in the non-display area NDA. The non-display area NDA may include a photo sensor array area PSAA.

In addition, the display panel 100 further includes an encapsulation layer 190 disposed over the display elements 103 to cover the display elements 103. The encapsulation layer 190 may prevent (or at least reduce) moisture, oxygen, etc., from being introduced into the display elements 103. The encapsulation layer 190 may be formed in a single layer, or may be formed in multiple layers.

The window 200 may be an outermost cover member disposed on an upper surface of the display panel 100 to protect a display surface of the display panel 100. The window 200 may cover a front surface of the display panel 100 and may be coupled to the display panel 100 via an adhesive layer 400. The adhesive layer 400 may be made of a resin-based material having optically high transparency, e.g., an optically clear resin (OCR), but exemplary embodiments are not limited thereto or thereby. The window 200 includes a display area DA corresponding to the display area DA of the display panel 100 and a non-display area NDA disposed outside the display area DA, e.g., surrounding the display area DA. The non-display area NDA of the window 200 may correspond to the non-display area NDA of the display panel 100.

A photo sensor array 300 may be disposed to correspond to the photo sensor array area PSAA of the base substrate 101, and may be provided on a surface (e.g., a rear surface) of the window 200. The surface of the window 200 may be a surface opposite the display panel 100. The photo sensor array 300 may extend along the second direction D2. The photo sensor array 300 may be disposed at at least one side of the non-display area NDA of the window 200 to correspond to the photo sensor array area PSAA of the display panel 100. The photo sensor array 300 may include a plurality of photo sensors (not shown) extending along the second direction D2 and a readout line (not shown) connected to each of the plurality of photo sensors. For instance, the plurality of photo sensors may be arranged in the same direction as the direction (e.g., the second direction D2) in which the data lines are arranged.

A fingerprint contact area FCA may be provided on another surface (e.g., a front surface) opposite to the surface of the window 200 upon which the photo sensor array 300 is disposed. The fingerprint contact area FCA is an area with which a finger of the user comes in contact (e.g., direct contact) with, for instance, the window 200. Fingerprint information of the user may be sensed through the photo sensor array 300. The fingerprint contact area FCA may be disposed in the display area DA of the window 200; however, exemplary embodiments are not limited thereto or thereby.

According to one or more exemplary embodiments, the photo sensor array 300 is disposed in the non-display area NDA of each of the window 200 and the display panel 100, but exemplary embodiments are not limited thereto or thereby. The photo sensor array 300 may be disposed in the display area DA of each of the window 200 and the display panel 100. In this manner, the fingerprint contact area FCA may be disposed in the display area DA adjacent to the photo sensor array 300 of the window 200.

Figure 5:
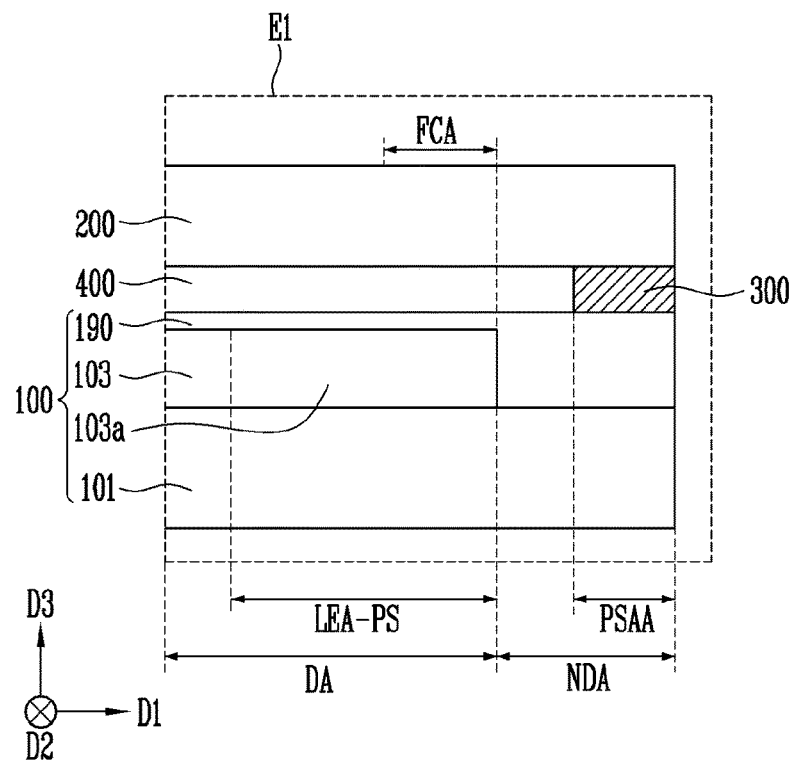
FIG. 5 is an enlarged sectional view of portion E1 of FIG. 4, according to one or more exemplary embodiments.
Figure 6:
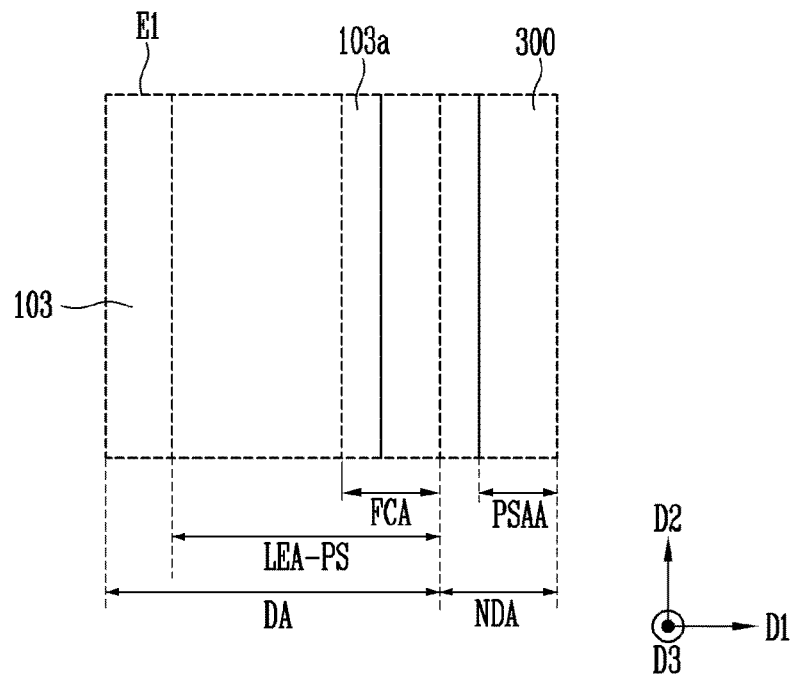
FIG. 6 is a plan view of the display device of FIG. 5, according to one or more exemplary embodiments.

FIG. 5 is an enlarged sectional view of portion E1 of FIG. 4, according to one or more exemplary embodiments. FIG. 6 is a plan view of the display device of FIG. 5, according to one or more exemplary embodiments. The "plan view" may be considered a "top-down" view of the display device of FIG. 5 when viewed in a direction opposite the third direction D3.

Referring to FIGS. 4 to 6, the display device includes a display panel 100 and a window 200 disposed on the display panel 100. The display device further includes a photo sensor array 300 provided between the display panel 100 and the window 200, and an adhesive layer 400 that couples the display panel 100 and the window 200 to one another. The display panel 100 includes a base substrate 101, display elements 103 provided on the base substrate 101, and an encapsulation layer 190 provided over the display elements 103.

Figure 11:
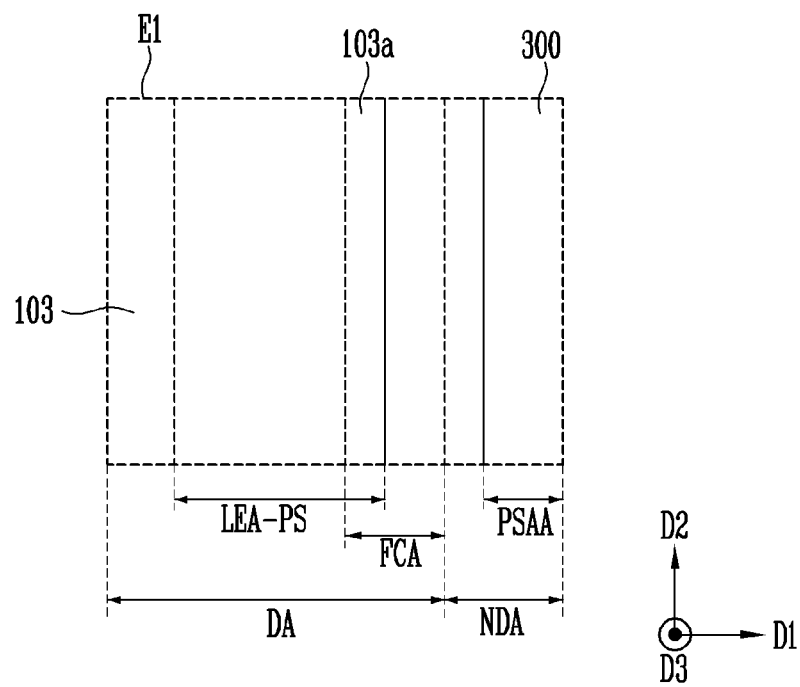
FIGS. 11, 12, 13, and 14 are plan views of display devices, according to various exemplary embodiments.

The base substrate 101 includes a display area DA and a non-display area NDA. The display area DA of the base substrate 101 includes a light emitting area LEA-PS for photo sensors. A plurality of pixels 103a adjacent to the photo sensor array 300 among the display elements 103 may be disposed in the light emitting area LEA-PS. For descriptive convenience, the plurality of pixels 103a adjacent to the photo sensor array 300 will be referred to as display elements 103a for the photo sensor array 300. Although the light emitting area LEA-PS for the photo sensor array 300 is shown in FIGS. 5 and 6 as extending to the boundary between the display area DA and the non-display area NDA, it is contemplated that the light emitting area LEA-PS for the photo sensor array 300 may not extend all the way to the boundary, such as illustrated in FIG. 11.

Each of the display elements 103a for the photo sensor array 300 includes an organic light emitting element that emits white light and/or colored light. In this manner, the display elements 103a for the photo sensor array 300 may be used as light sources and the photo sensor array 300 may sense fingerprint information of a finger of a user.

Figure 14:
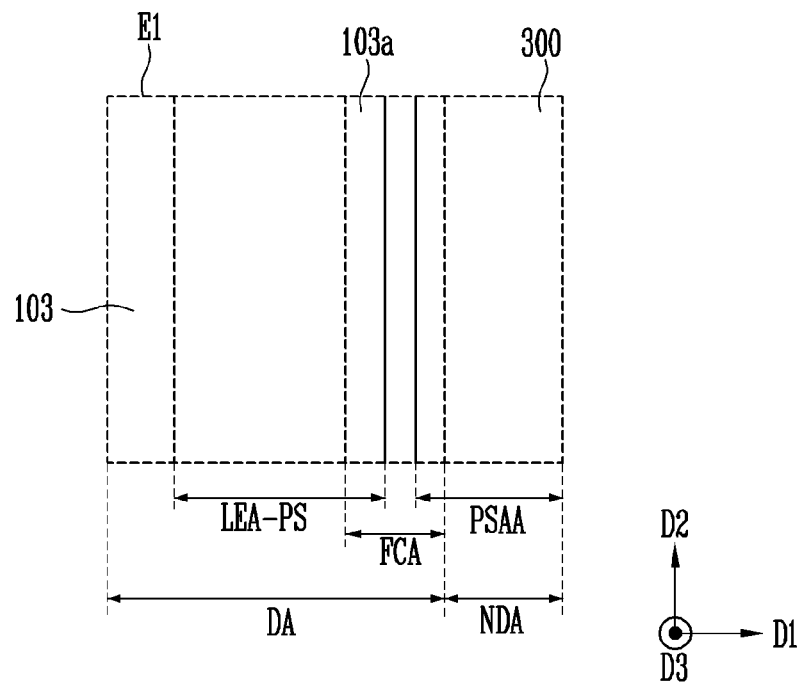

The non-display area NDA of the base substrate 101 includes a photo sensor array area PSAA corresponding to the photo sensor array 300. According to one or more exemplary embodiments, the photo sensor array area PSAA may also overlap a portion of the display area DA, such as illustrated in FIG. 14. The photo sensor array 300 is provided on one surface of the window 200. For instance, the photo sensor array 300 may be provided between the window 200 and the display panel 100. The photo sensor array 300 may include a plurality of photo sensors disposed along the same direction as the driving direction of the display elements 103a for the photo sensor array 300 and a readout line (not shown) connected to each of the plurality of photo sensors. For instance, the plurality of photo sensors may be arranged in the same direction as the direction (e.g., the second direction D2) in which the data lines are arranged.

Figure 12:
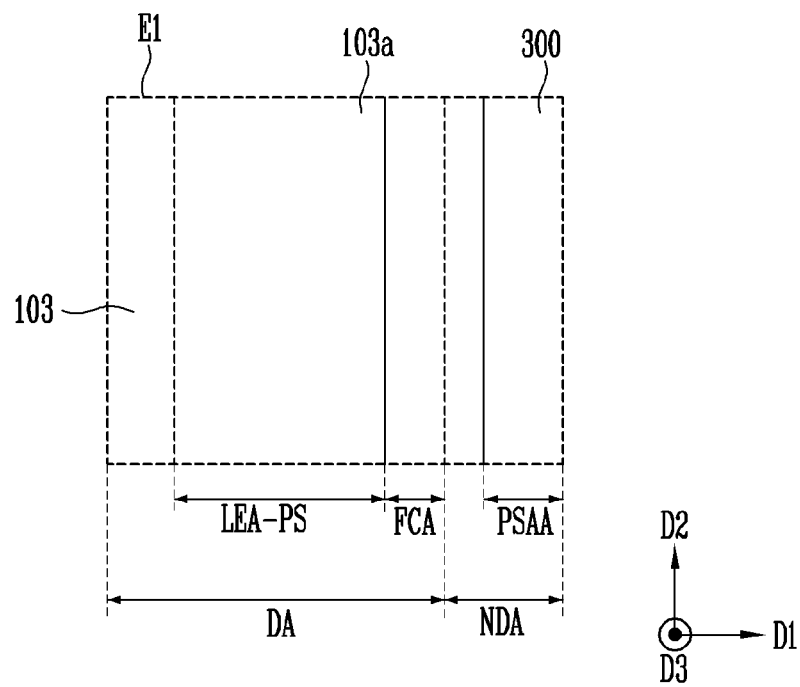
Figure 13:
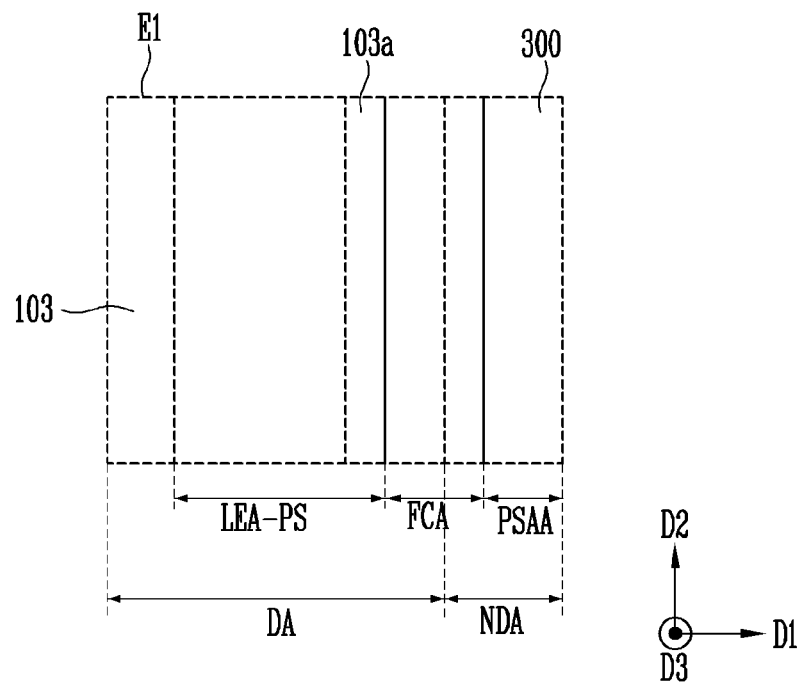

The window 200 includes a fingerprint contact area FCA. The fingerprint contact area FCA may be provided on the other surface (e.g., upper surface) that is opposite to the surface of the window 200 on which the photo sensor array 300 is disposed. The fingerprint contact area FCA is disposed on the other surface of the window 200 to correspond to a portion of the display area DA of the base substrate 101. Also, the fingerprint contact area FCA may be provided between the display area DA and the non-display area NDA of the base substrate 101 on the other surface of the window 200. For instance, the fingerprint contact area FCA may overlap one or more of the display area DA and the non-display area NDA. For example, one side of the fingerprint contact area FCA may be disposed adjacent to the photo sensor array 300 and another side of the fingerprint contact area FCA may overlap with a portion of the light emitting area LEA-PS. As another example, one side of the fingerprint contact area FCA may terminate at a boundary between the display area DA and the non-display area NDA, and another side of the fingerprint contact area FCA may overlap the display area DA, but terminate at a boundary of the light emitting area LEA-PS of the photo sensor array 300, such as illustrated in FIG. 12. As yet another example, one side of the fingerprint contact area FCA may overlap the display area DA and another side of the fingerprint contact area FCA may overlap the non-display area NDA, such as illustrated in FIG. 13.

When a finger of the user comes in contact with the fingerprint contact area FCA, the display device may perform a function for sensing fingerprint information of the user. In this manner, the display elements 103a for the photo sensor array 300 may be driven to emit white light and/or colored light along the second direction D2 according to data signals provided to the display elements 103a for the photo sensor array 300. The light emitted from each of the display elements 103a for the photo sensor array 300 may be reflected by the finger of the user that interacts with the fingerprint contact area FCA. The reflected light may be supplied to the photo sensor array 300. The photo sensor array 300 may sense fingerprint information of the finger of the user using the light emitted from the display elements 103a for the photo sensor array 300, such as the reflected light.

According to one or more exemplary embodiments, the display elements 103a for the photo sensor array 300 are used as light sources for the photo sensor array 300, and, as such, a separate light source for sensing the fingerprint information of a finger of the user may not be provided. In addition, given that the display elements 103a for the photo sensor array 300 used as light sources of the photo sensor array 300 may be arranged in an area adjacent to the photo sensor array 300, the amount of light emitted from the display elements 103a for the photo sensor array 300 that reaches the photo sensor array 300 may be sufficient even at relatively low levels. In this manner, a light receiving efficiency of the photo sensor array 300 may improve the sensitivity of sensing the fingerprint information of the finger of the user may increase.

In comparison with a conventional display device including a fingerprint sensing element assembled to an exterior portion of a display panel (or the exterior portion of the conventional display device), the photo sensor array 300 is disposed in the non-display area NDA of the base substrate 101. In this manner, one or more exemplary embodiments minimize (or at least reduce) spatial limitations for a fingerprint sensing element.

Figure 7A:
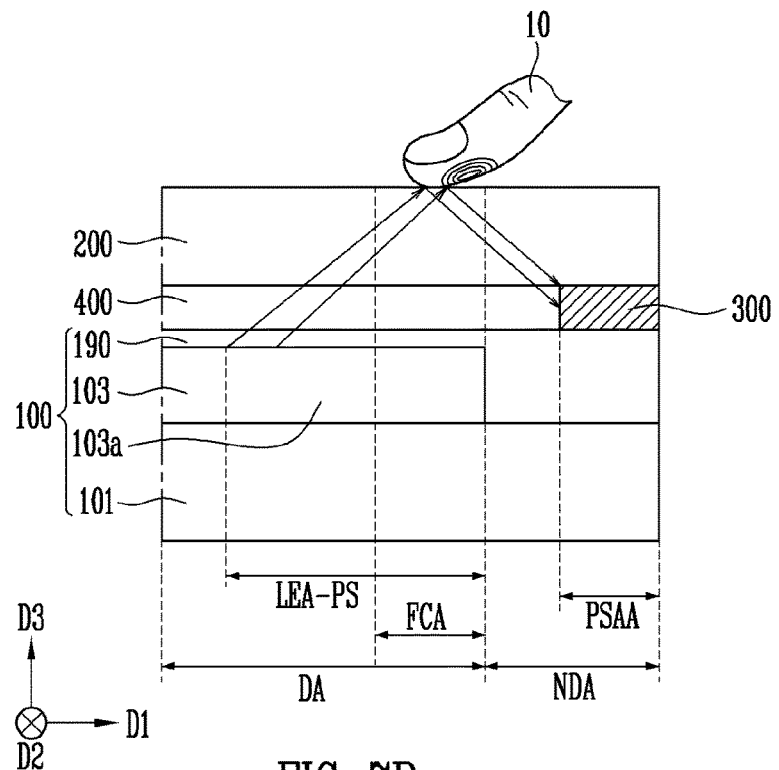
FIG. 7A is a cross-sectional view of the display device of FIG. 6 illustrating a method for sensing a fingerprint, according to one or more exemplary embodiments.
Figure 7B:
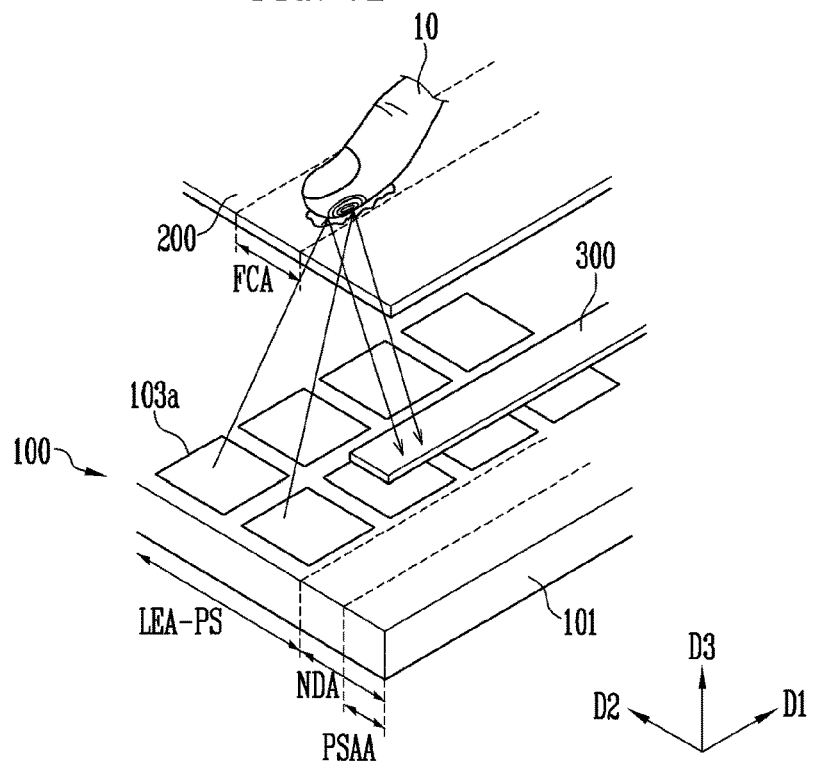
FIG. 7B is an exploded perspective view of the display device of FIG. 7A illustrating the method for sensing a fingerprint, according to one or more exemplary embodiments.
Figure 8:
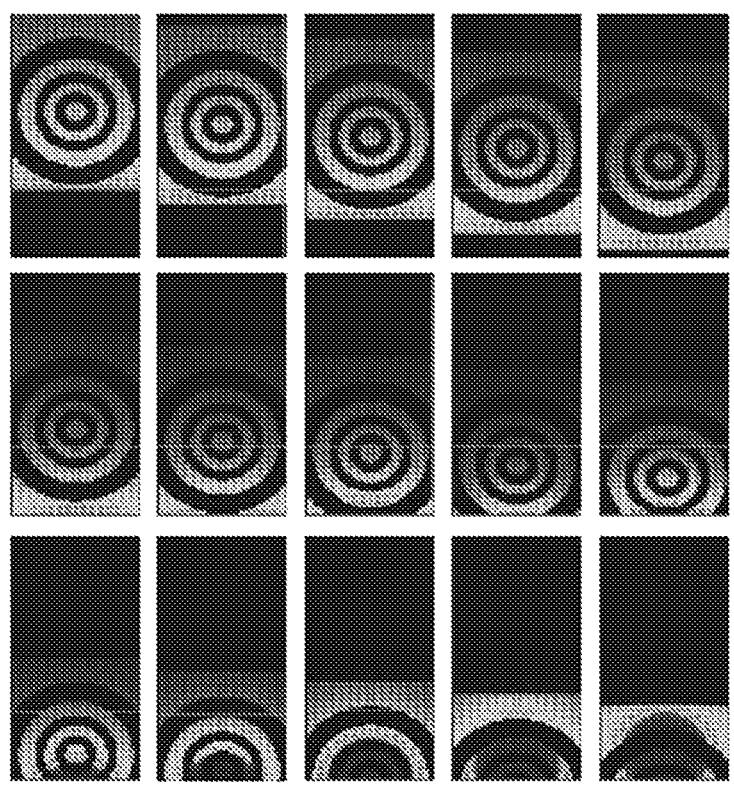
FIG. 8 provides simulation results illustrating fingerprint information of a user that is sensed through a photo sensor array of the display device of FIGS. 7A and 7B, according to one or more exemplary embodiments.

FIG. 7A is a cross-sectional view of the display device of FIG. 6 illustrating a method for sensing a fingerprint, according to one or more exemplary embodiments. FIG. 7B is an exploded perspective view of the display device of FIG. 7A illustrating the method for sensing a fingerprint, according to one or more exemplary embodiments. FIG. 8 provides simulation results illustrating fingerprint information of a user that is sensed through a photo sensor array of the display device of FIGS. 7A and 7B, according to one or more exemplary embodiments.

Referring to FIGS. 2, 6, 7A, and 7B, the display device includes a display panel 100, a window 200, and a photo sensor array 300. Also, the display device may further include a control unit 102 that controls fingerprint sensing and/or image display. The control unit 102 may control fingerprint sensing and/or image display based on one or more sequences of one or more instructions that may be stored in one or more memories (not illustrated) and executed in association with components of the display panel 100 and the photo sensor array 300. The one or more memories may be any medium (e.g., non-volatile media, volatile media, transmission media, etc.) that participates in providing the one or more sequences of one or more instructions (e.g., computer code) to one or more software, hardware, and/or firmware components. For instance, the one or more sequences of one or more instructions may be executable by one or more general purpose and/or special purpose components of the control unit 102. For example, the one or more general purpose and/or special purpose components may include one or more discrete circuits, digital signal processing chips, integrated circuits, application specific integrated circuits, microprocessors, processors, programmable arrays, field programmable arrays, instruction set processors, and/or the like.

According to one or more exemplary embodiments, a finger 10 of a user may come in contact with a fingerprint contact area FCA of the window 200. As such, the display elements 103a for the photo sensor array 300 disposed in a light emitting area LEA-PS may be used as light sources for photo sensors of the photo sensory array 300. In one or more exemplary embodiments, if the finger 10 of the user does not come in contact with the fingerprint contact area FCA, the light emitting area LEA-PS for the photo sensors may display an image as a display area DA of the display panel 100. Additionally, when the finger 10 of the user does not come in contact with the fingerprint contact area FCA, the fingerprint contact area FCA may display the image as a display area DA of the window 200.

In one or more exemplary embodiments, the image may provide information to the user to inform the user of the existence and/or position of the fingerprint contact area FCA. It is also contemplated that the image may inform the user of a function (e.g., fingerprint sensing function) that is executable in association with the fingerprint contact area FCA. In one or more exemplary embodiments, the image may be selectively displayed, such as, in response to the detection of a hovering (or almost contacting) interaction of the finger 10 with the display device, the display of an idle (or home) screen of the display device, such as to unlock an electronic device including the display device, and/or the like. Exemplary embodiments, however, are not limited thereto or thereby. In this manner, when the aforementioned image is not presented, other display information (normal display content) may be presented, such as content corresponding to data provided from an image source, such as an external image source.

Light emitted from the display elements 103a for the photo sensor array 300 may reach the finger 10 of the user and then may be reflected from the finger 10 of the user and made incident on the photo sensor array 300. The photo sensor array 300 may sense fingerprint information of the finger 10 of the user using the incident light. In response to the fingerprint information of the finger 10 of the user being sensed by the photo sensor array 300, the fingerprint of the user may be registered and/or stored as fingerprint information. In one or more exemplary embodiments, the control unit 102 may control the display device to display an image on the display panel 100, such as an image of the detected fingerprint information, an image confirming detection of the fingerprint of the user, and/or the like.

The display elements 103a for the photo sensor array 300 may be arranged in a matrix formation including one or more rows and columns of display elements 103a in the light emitting area LEA-PS for the photo sensor array 300. As such, when the finger 10 of the user comes in contact with the fingerprint contact area FCA, the display elements 103a for the photo sensor array 300 may be used as a light source that may be driven (e.g., sequentially driven) in the second direction D2. The photo sensor array 300 may include a plurality of photo sensors (not shown) arranged (e.g., spaced apart from one another) along the second direction D2 on the rear surface of the window 200. For instance, each of the plurality of photo sensors may be disposed in the same line as the display elements 103a (or in correspondence with respective display elements 103a) for the photo sensor array 300. Exemplary embodiments, however, are not limited thereto or thereby.

According to one or more exemplary embodiments, when the finger 10 of a user comes in contact with a portion of the fingerprint contact area FCA, the display elements 103a arranged in the light emitting area LEA-PS for the photo sensor array 300 under the area that the finger 10 of the user comes in contact may be used as a light source driven (e.g., sequentially driven) along the second direction D2, thereby emitting light. Light emitted from the display elements 103a may be reflected by the finger 10 of the user and provided to a photo sensor disposed on the same line as the display element 103a that emitted the light that was reflected and detected by the photo sensor. The photo sensor and/or the control unit 102 may sense fingerprint information of the finger 10 of the user that contacted the fingerprint contact area FCA using the incident light. As such, when the arrangement direction of the display elements 103a for the photo sensor array 300 that area sequentially driven along the second direction D2 and the arrangement direction of the plurality of photo sensors of the photo sensor array 300 are equal to one another, the fingerprint information of the finger 10 of the user, as shown in FIG. 8, may be sequentially sensed along the second direction D2.

Although the display elements 103a for the photo sensor array 300 have been described as being sequentially driven in the second direction D2, exemplary embodiments are not limited thereto or thereby. For example, the display elements 103a for the photo sensor array 300 may be sequentially driven in the first direction D1 or in any other suitable fashion.

Figure 9:
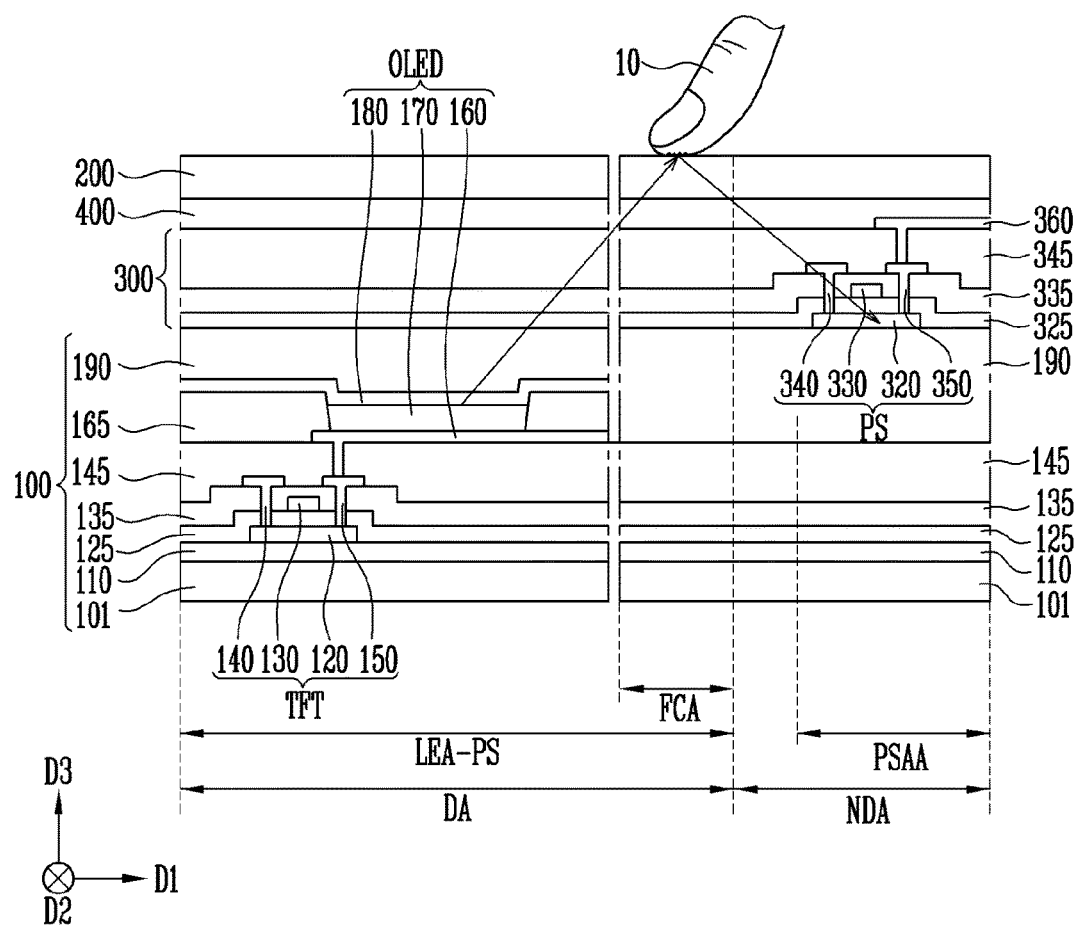
FIG. 9 is a cross-sectional view of a light emitting area for photo sensors of a photo sensor array, a fingerprint contact area, and a photo sensor array area of the display device of FIG. 5, according to one or more exemplary embodiments.

FIG. 9 is a cross-sectional view of a light emitting area for photo sensors of a photo sensor array, a fingerprint contact area, and a photo sensor array area of the display device of FIG. 5, according to one or more exemplary embodiments.

Although a plurality of display elements 103a are arranged in the light emitting area LEA-PS of the photo sensor array 300, FIG. 9 merely illustrates one display element 103a for illustrative and descriptive convenience. Also, the display device may include a touch array, such as a touch detection layer including detection electrodes, but the illustration of the touch array is omitted in FIG. 9 to avoid obscuring exemplary embodiments. It is noted, however, that the touch array may form a portion (e.g., one or more layers) of display panel 100 or may be coupled to display panel 100. For instance, the touch array may be disposed between window 200 and display panel 100, between adhesive layer 400 and encapsulation layer 190, between encapsulation layer 190 and substrate 101, etc.

Referring to FIGS. 5 and 9, the display device includes a display panel 100, a window 200 disposed on a surface (e.g., upper surface) of the display panel 100, and a photo sensor array 300 disposed between the display panel 100 and the window 200. The display panel 100 includes a base substrate 101 including a display area DA and a non-display area NDA. The display area DA of the base substrate 101 may include a light emitting area LEA-PS for a photo sensor array 300, and the non-display area NDA of the base substrate 101 may include a photo sensor array area PSAA in which the photo sensor array 300 is disposed. The window 200 includes a fingerprint contact area FCA with which a finger 10 of a user comes in contact.

A thin film transistor TFT, an organic light emitting element OLED connected to the thin film transistor TFT, and an encapsulation layer 190 covering the organic light emitting element OLED may be provided in the light emitting area LEA-PS for the photo sensor array 300 of the base substrate 101. The thin film transistor TFT and the organic light emitting element OLED may constitute display elements for a first photo sensor array among display elements 103a for the photo sensor array 300. The display elements 103a are arranged in the light emitting area LEA-PS for the photo sensor array 300.

The base substrate 101 includes a transparent insulating material to enable light to be transmitted therethrough. The base substrate 101 may be a rigid substrate. For example, the base substrate 101 may be one of a glass base substrate, a quartz base substrate, a glass ceramic base substrate, and a crystalline glass base substrate. It is also contemplated that the base substrate 101 may be a flexible substrate. In this manner, the base substrate 101 may be one of a film base substrate including an organic polymer material and a plastic base substrate. For example, the base substrate 101 may include one of polystyrene, polyvinyl alcohol, polymethyl methacrylate, polyethersulfone, polyacrylate, polyetherimide, polyethylene naphthalate, polyethylene terephthalate, polyphenylene sulfide, polyarylate, polyimide, polycarbonate, triacetate cellulose, and cellulose acetate propionate. In addition, the base substrate 101 may include a fiber glass reinforced plastic (FRP). Exemplary embodiments are not limited thereto or thereby. To this end, the material of the base substrate 101 has resistance (e.g., heat resistance) against high processing temperature(s) in a fabricating process of the display device.

The thin film transistor TFT includes a first active pattern 120, a first gate electrode 130, a first source electrode 140, and a first drain electrode 150. The first active pattern 120 may be disposed on the base substrate 101. The first active pattern 120 may include any one of amorphous silicon (a-Si), polycrystalline silicon (p-Si), oxide semiconductor, and organic semiconductor. The oxide semiconductor may include at least one of zinc (Zn), indium (In), gallium (Ga), tin (Sn), and mixtures thereof. For example, the oxide semiconductor may include indium-gallium-zinc oxide (IGZO).

The active pattern 120 includes a source region connected to the first source electrode 140, a drain region connected to the first drain electrode 150, and a channel region provided between the source region and the drain region. The source region and the drain region may be regions in which impurities are doped or injected. Although not shown in FIG. 9, when the first active pattern 120 includes the oxide semiconductor, a light blocking layer may be provided on each of the top and bottom surfaces of the first active pattern 120. The light blocking layer may block light introduced to the first active pattern 120.

A buffer layer 110 may be disposed between the base substrate 101 and the first active pattern 120. The buffer layer 110 may include at least one of silicon oxide ($SiO_x$) and silicon nitride ($SiN_x$). For example, the buffer layer 110 may include a first layer including silicon oxide, and a second layer disposed on the first layer, the second layer including silicon nitride. Also, the buffer layer 110 may include silicon oxynitride (SiON). The buffer layer 110 may be an organic insulating layer including an organic material. In one or more exemplary embodiments, the buffer layer 110 prevents (or at least reduces) impurities from being diffused and penetrated into the thin film transistor TFT from the base substrate 101, thereby preventing (or reducing) deterioration of electrical characteristics of the thin film transistor TFT.

A gate insulating layer 125 may be provided over the first active pattern 120. The gate insulating layer 125 may insulate the first active pattern 120 and the first gate electrode 130 from each other. The gate insulating layer 125 may include at least one of silicon oxide ($SiO_x$) and silicon nitride ($SiN_x$).

The first gate electrode 130 may be disposed on the gate insulating layer 125 to cover a region corresponding to the channel region of the first active pattern 120. The first gate electrode 130 may be made of at least one metal, such as gold (Au), silver (Ag), aluminum (Al), molybdenum (Mo), chromium (Cr), titanium (Ti), nickel (Ni), neodymium (Nd) and copper (Cu), or alloys thereof. The first gate electrode 130 may be formed in a single layer; however, exemplary embodiments are not limited thereto or thereby. For instance, the first gate electrode 130 may be formed in a multi-layered structure in which at least two materials among the metals and the alloys are stacked.

An interlayer insulating layer 135 may be provided over the first gate electrode 130. The interlayer insulating layer 135 may be an inorganic insulating layer made of an inorganic material. The inorganic material may include at least once of silicon oxide, silicon nitride, silicon oxynitride, and the like.

The first source electrode 140 and the first drain electrode 150 may be provided on the interlayer insulating layer 135. The first source electrode 140 and the first drain electrode 150 may be insulated from the first gate electrode 130 by the interlayer insulating layer 135. The first source electrode 140 is connected to the source region through an opening passing through the gate insulating layer 125 and the interlayer insulating layer 135, and the first drain electrode 150 is connected to the drain region through an opening passing through the gate insulating layer 125 and the interlayer insulating layer 135.

The first source electrode 140 and the first drain electrode 150 may be made of a metal. For example, the first source electrode 140 and the first drain electrode 150 may be made of at least one metal, such as gold (Au), silver (Ag), aluminum (Al), molybdenum (Mo), chromium (Cr), titanium (Ti), nickel (Ni), neodymium (Nd) and copper (Cu), or alloys thereof. In addition, each of the first source electrode 140 and the first drain electrode 150 may be formed in a single layer; however, exemplary embodiments are not limited thereto or thereby. For instance, the first source electrode 140 and the first drain electrode 150 may be formed in a multi-layered structure with at least two materials among the metals and the alloys being stacked.

Although the thin film transistor TFT has been described as including a top gate structure, exemplary embodiments are not limited thereto or thereby. For example, the thin film transistor TFT may include a bottom gate structure, a multi-gate structure, etc.

A first protective layer 145 may be disposed over the thin film transistor TFT. The first protective layer 145 covers the thin film transistor TFT, and may include at least one layer. The first protective layer 145 reduces bending of a lower structure and planarizes a surface of the underlying structure. The first protective layer 145 includes a contact hole through which a portion of the first drain electrode 150 is exposed. The first protective layer 145 may be an organic insulating layer made of an organic material. The organic material may include fluorine-based carbon compounds, such as polyacryl, polyimide, and Teflon, and organic insulating materials, such as polyepoxy and benzocyclobutene.

The organic light emitting element OLED, which is connected to the first drain electrode 150, may be disposed on the first protective layer 145. The organic light emitting element OLED may include a first electrode 160 connected to the first drain electrode 150, an organic layer 170 disposed on the first electrode 160, and a second electrode 180 disposed on the organic layer 170. One of the first electrode 160 and the second electrode 180 may be an anode electrode, and the other of the first electrode 160 and the second electrode 180 may be a cathode electrode. For example, the first electrode 160 may be an anode electrode, and the second electrode 180 may be a cathode electrode.

According to one or more exemplary embodiments, at least one of the first electrode 160 and the second electrode 180 may be a transmissive electrode. For example, when the organic light emitting element OLED is a bottom emission type organic light emitting element, the first electrode 160 may be a transmissive electrode, and the second electrode 180 may be a reflective electrode. When the organic light emitting element OLED is a top emission type organic light emitting element, the first electrode 160 may be a reflective electrode, and the second electrode 180 may be a transmissive electrode. When the organic light emitting element OLED is a double-sided emission type organic light emitting element, both the first electrode 160 and the second electrode 180 may be transmissive electrodes. For convenience, exemplary embodiments will be described including the first electrode 160 as an anode electrode and the organic light emitting element OLED as a top emission type organic light emitting element.

The first electrode 160 may be disposed on the first protective layer 145. The first electrode 160 may include a reflective layer (not shown) capable of reflecting light and a transparent conductive layer (not shown) disposed on the top or bottom of the reflective layer. At least one of the reflective layer and the transparent conductive layer may be connected to the first drain electrode 150 of the thin film transistor TFT. The reflective layer may include a material capable of reflecting light. For example, the reflective layer may include at least one of aluminum (Al), silver (Ag), chromium (Cr), molybdenum (Mo), platinum (Pt), nickel (Ni), and alloys thereof. Exemplary embodiments, however, are not limited thereto or thereby. The transparent conductive layer may include a transparent conductive oxide. For example, the transparent conductive layer may include at least one transparent conductive oxide among indium tin oxide (ITO), indium zinc oxide (IZO), aluminum zinc oxide (AZO), gallium doped zinc oxide (GZO), zinc tin oxide (ZTO), gallium tin oxide (GTO), and fluorine doped tin oxide (FTO). Exemplary embodiments, however, are not limited thereto or thereby.

A pixel defining layer 165 may be disposed on the first electrode 160 and the first protective layer 145. The pixel defining layer 165 may expose a portion of the first electrode 160 therethrough. For example, the pixel defining layer 165 may have a shape covering an edge of the first electrode 160 and the protective layer 145.

The organic layer 170 may have a multi-layered thin film structure at least including an emitting layer (EML). For example, the organic layer 170 may include a hole injection layer (HIL) for injecting holes, a hole transport layer (HTL) having a relatively excellent hole transporting property (the HTL may increase opportunity for holes and electrons to be re-combined by suppressing movement of electrons that fail to be combined in the EML and the EML may emit light through the re-combination of injected electrons and holes), an electron transport layer (ETL) providing relatively smooth transportation of electrons to the EML, and an electron transport layer (EIL) for injecting electrons. The color of light generated in the EML may be one of red, green, blue, and white, but exemplary embodiments are not limited thereto or thereby. For example, the color of light generated in the EML of the organic layer 170 may be one of magenta, cyan, yellow, etc.

The second electrode 180 may be disposed on the organic layer 170. The second electrode 180 may include a material having a relatively low work function as compared with the first electrode 160. For example, the second electrode 180 may include at least one of tungsten (W), molybdenum (Mo), silver (Ag), magnesium (Mg), aluminum (Al), platinum (Pt), palladium (Pd), gold (Au), nickel (Ni), neodymium (Nd), iridium (Jr), chromium (Cr), lithium (Li), calcium (Ca), and alloys thereof. Exemplary embodiments, however, are not limited thereto or thereby.

The encapsulation layer 190 may isolate the organic light emitting element OLED from an external environment. For instance, the encapsulation layer 190 may hermetically seal the organic light emitting element OLED from an ambient environment. In this manner, the encapsulation layer 190 may be disposed on the second electrode 180 to prevent (or at least reduce) moisture and oxygen from penetrating into the organic light emitting element OLED.

In one or more exemplary embodiments, the encapsulation layer 190 may be a thin film encapsulation layer including a plurality of inorganic layers (not shown) and a plurality of organic layers (not shown), which cover the organic light emitting element OLED. For example, the encapsulation layer 190 may have a structure in which the inorganic layers and the organic layers are alternately stacked with one another. In addition, the lowermost and uppermost layers of the encapsulation layer 190 may be inorganic layers. The inorganic layer may include at least one of silicon oxide ($SiO_x$), silicon nitride ($SiN_x$), silicon oxynitride (SiON), aluminum oxide ($Al_2O_3$), titanium oxide ($TiO_2$), zirconium oxide (ZrOx), and tin oxide (ZnO).

The display element for the first photo sensor array includes the thin film transistor TFT and the organic light emitting element OLED. The display element generates light to be used as a light source for the photo sensor array 300 when the finger 10 of the user comes in contact with the fingerprint contact area FCA. For instance, the control unit 102 may detect contact of the finger 10 with window 200, and, thereby, control the display element to illuminate a portion of the finger 10 with illumination. It is noted that the illumination utilized to illuminate the portion of the finger 10 may be different that illumination utilized to form an image via the display device. At least some of the light generated in the display element for the first photo sensor array may be reflected by the finger 10 of the user to advance toward the photo sensor array 300.

The photo sensor array 300 may be provided on the encapsulation layer 190. The photo sensor array 300 may include a photo sensor PS and a readout line 360 connected to the photo sensor PS. The photo sensor PS may be an optical detection thin film transistor. For instance, the photo sensor PS may include a second active pattern 320, a second gate electrode 330, a second source electrode 340, and a second drain electrode 350.

The second active pattern 320 may be disposed on the encapsulation layer 190. The second active pattern 320 includes a source region connected to the second source electrode 340, a drain region connected to the second drain electrode 350, and a channel region provided between the source region and the drain region. The source region and the drain region may be regions in which impurities are doped or injected.

A first photo sensor insulating layer 325 may be provided over the second active layer 320. The first photo sensor insulating layer 325 may insulate the second active pattern 320 and the second gate electrode 330 from each other. The first photo sensor insulating layer 325 may include at least one of silicon oxide ($SiO_x$) and silicon nitride ($SiN_x$). The second gate electrode 330 may be disposed on the first photo sensor insulating layer 325 to cover a region corresponding to the channel region of the second active pattern 320.

A second photo sensor insulating layer 335 may be provided over the second gate electrode 330. The second photo sensor insulating layer 335 may be an inorganic insulating layer made of an inorganic material. The inorganic material may include silicon nitride ($SiN_x$), silicon oxide ($SiO_x$), silicon oxynitride (SiON), and the like.

The second source electrode 340 and the second drain electrode 350 may be provided on the second photo sensor insulating layer 335. The second source electrode 340 and the second drain electrode 350 may be insulated from the second gate electrode 330 by the second photo sensor insulating layer 335. The second source electrode 340 is connected to the source region through a first opening passing through the first and second photo sensor insulating layers 325 and 335, and the second drain electrode 350 is connected to the drain region through a second opening passing through the first and second photo sensor insulating layers 325 and 335.

A second protective layer 345 may be disposed over the photo sensor PS. The second protective layer 345 includes a contact hole through which a portion of the second drain electrode 350 is exposed. The second protective layer 345 may be an organic insulating layer made of an organic material. The readout line 360 may be disposed on the second protective layer 345. The readout line 360 may be connected to an external driving unit (not shown), to provide fingerprint information of the finger 10 of the user, sensed by the photo sensor PS.

The photo sensor PS senses fingerprint information of the finger 10 of the user using light that is emitted from the display element for the first photo sensor array and then reflected by the finger 10 of the user to be incident into the photo sensor PS. In one or more exemplary embodiments, the photo sensor PS may sense three-dimensional pattern information corresponding to a three-dimensional pattern on an object interacting with the fingerprint detection area FCA. For instance, the three-dimensional pattern may correspond to a epidermal ridges of a human appendage, protrusions of a three-dimensional bar code, etc.

According to one or more exemplary embodiments, the photo sensor array 300 is disposed on the top of the display element for the first photo sensor array; however, exemplary embodiments are not limited thereto or thereby. For example, the photo sensor array 300 may be provided in the same layer as the display element for the first photo sensor array. This will be described in more detail with reference to FIG. 10.

Figure 10:
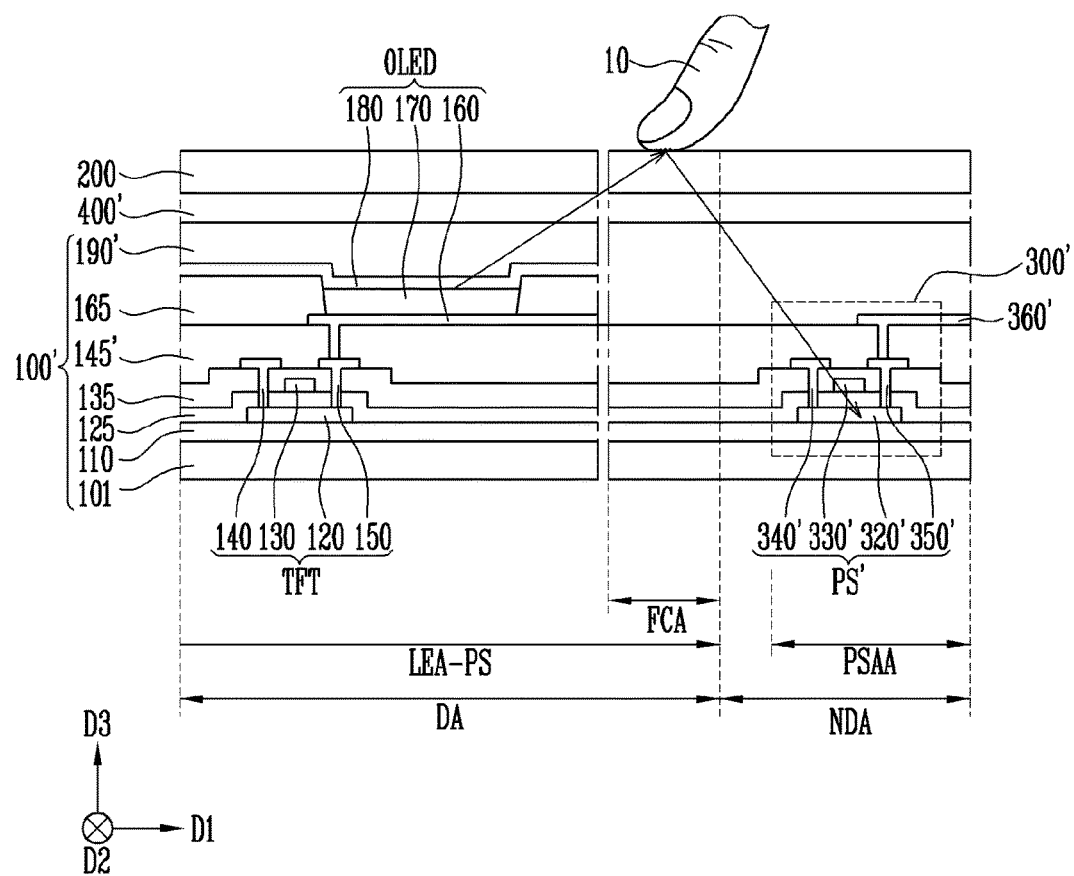
FIG. 10 is a cross-sectional view of a light emitting area for photo sensors of a photo sensor array, a fingerprint contact area, and a photo sensor array area of the display device of FIG. 5, according to one or more exemplary embodiments.

FIG. 10 is a cross-sectional view of a light emitting area for photo sensors of a photo sensor array, a fingerprint contact area, and a photo sensor array area of the display device of FIG. 5, according to one or more exemplary embodiments. The display device of FIG. 10 may be similar to the display device of FIG. 9, and, as such, differences from the display device of FIG. 9 will mainly be described to avoid redundancy. Portions not described in association with FIG. 10 may correspond to portions described in association with FIG. 9. As such, identical reference numerals designate identical components, and similar reference numerals designate similar components.

Referring to FIG. 10, the display device includes a display panel 100', a window 200 disposed on a surface (e.g., upper surface) of the display panel 100', and a photo sensor array 300' disposed between a base substrate 101 of the display panel 100' and the window 200. The base substrate 101 includes a display area DA and a non-display area NDA. The display area DA of the base substrate 101 may include a light emitting area LEA-PS for the photo sensor array 300', and the non-display area NDA of the base substrate 101 may include a photo sensor array area PSAA over which the photo sensor array 300' is disposed. The adhesive layer 400' may couple the window 200 with the display panel 100', and, as such, may be disposed between an encapsulation layer 190' of the display panel 100' and the window 200.

A thin film transistor TFT, an organic light emitting element OLED connected to the thin film transistor TFT, and an encapsulation layer 190' covering the organic light emitting element OLED may be provided in the light emitting area LEA-PS for the photo sensor array 300 of the base substrate 101. It is noted that the encapsulation layer 190' may also cover the photo sensor array 300'. The thin film transistor TFT and the organic light emitting element OLED may constitute a display element for a first photo sensor array among display elements 103a for the photo sensor array 300'. The display elements 103a are arranged in the light emitting area LEA-PS for the photo sensor array 300'.

The window 200 includes a fingerprint contact area FCA with which a finger 10 of a user comes in contact. The photo sensor array 300' includes a photo sensor PS' and a readout line 360' connected to the photo sensor PS'. The photo sensor PS' may include a second active pattern 320', a second gate electrode 330', a second source electrode 340', and a second drain electrode 350'. The second active pattern 320' of the photo sensor PS' may be disposed in the same layer and formed through the same process as a first active pattern 120 of the display element for the first photo sensor array.

The second gate electrode 330' of the photo sensor PS' may be disposed in the same layer and formed through the same process of a first gate electrode 130 of the display element for the first photo sensor array. The second source electrode 340' and the second drain electrode 350' of the photo sensor PS' may be disposed in the same layer and formed through the same process as a first source electrode 140 and a first drain electrode 150 of the display element for the first photo sensor array.

A protective layer 145' may be disposed over the photo sensor PS'. The protective layer 145' includes openings that respectively expose a portion of the first drain electrode 150 of the display element for the first photo sensor array and a portion of the second drain electrode 350' of the photo sensor PS' therethrough. The first drain electrode 150 is electrically connected to the organic light emitting element OLED through the opening of the protective layer 145', and the second drain electrode 350' is electrically connected to the readout line 360' through the opening of the protective layer 145'.

The photo sensor PS' senses fingerprint information of the finger 10 of the user using light that is emitted from the display element for the first photo sensor array and then reflected by the finger 10 of the user to be incident with the photo sensor PS'.

According to one or more exemplary embodiments, a photo sensor array (or matrix) to detect three dimensional pattern (e.g., epidermal ridge) information may be arranged in a display area DA of a display device, as will become more apparent below in association with FIGS. 15-19. In this manner, a photo sensor array area and a fingerprint contact area may also be disposed in the display area DA.

Figure 15:
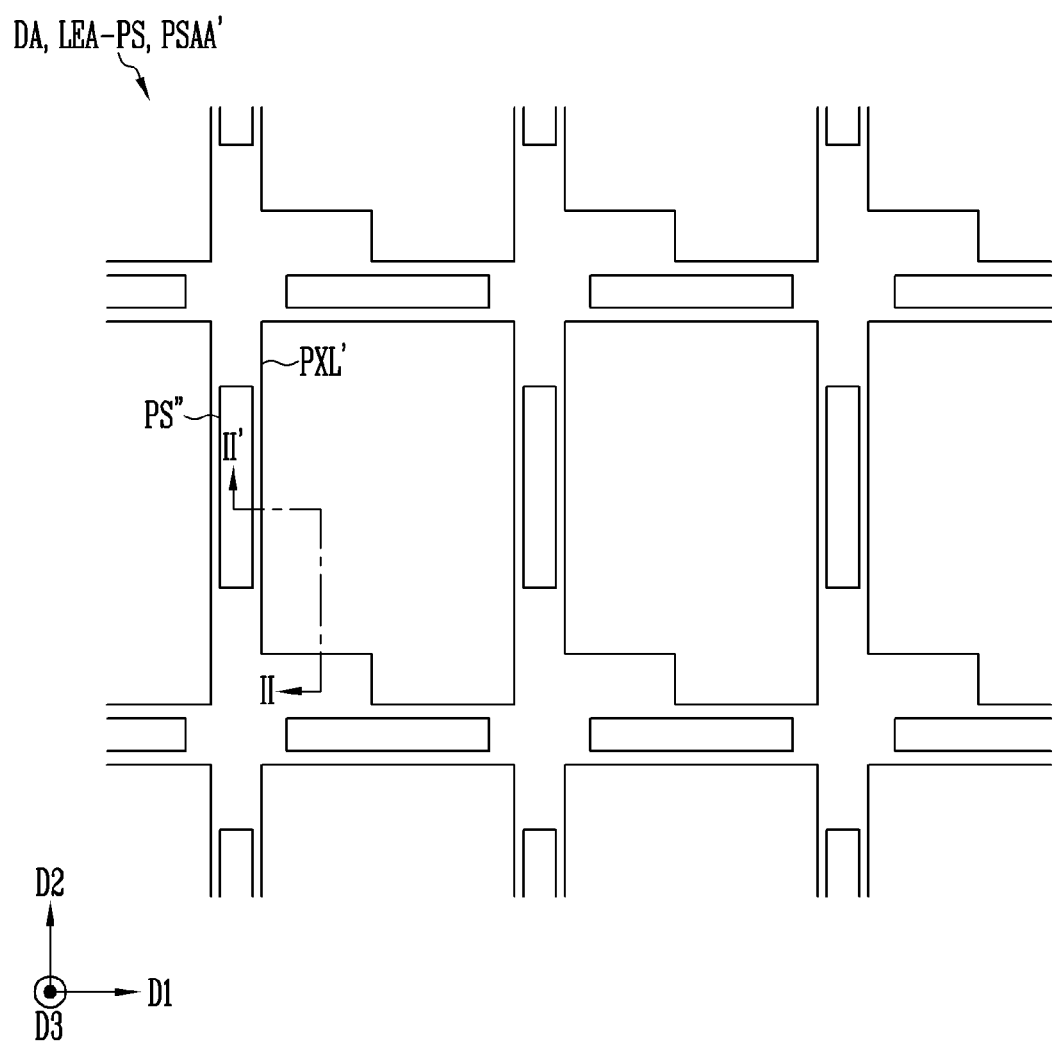
FIG. 15 is an enlarged plan view of a portion of a display device, according to one or more exemplary embodiments.
Figure 16:
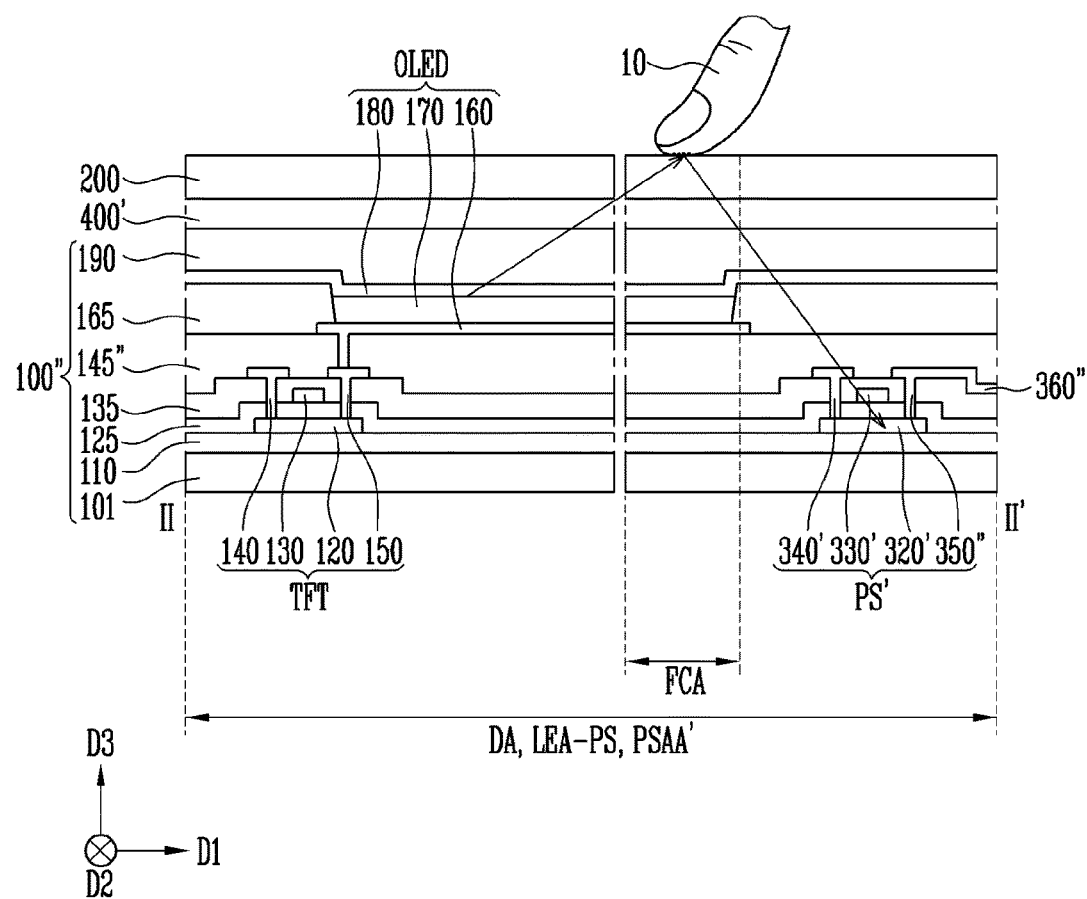
FIG. 16 is a cross-sectional view of the display device of FIG. 15 taken along sectional line II-II', according to one or more exemplary embodiments.

FIG. 15 is an enlarged plan view of a portion of a display device, according to one or more exemplary embodiments. FIG. 16 is a cross-sectional view of the display device of FIG. 15 taken along sectional line II-II', according to one or more exemplary embodiments. The display panel 100" (and, thereby, the display device) of FIGS. 15 and 16 may be similar to the display panels and display devices of FIGS. 9 and 10, and, as such, differences from the display panels and display devices of FIGS. 9 and 10 will mainly be described to avoid redundancy. To this end, portions not described in association with FIGS. 15 and 16 may correspond to portions described with respect to at least one of FIGS. 9 and 10. Identical reference numerals designate identical components, and similar reference numerals designate similar components.

Referring to FIGS. 15 and 16, the display device includes a display panel 100", a window 200 disposed on a surface (e.g., upper surface) of the display panel 100", and a photo sensor array. The display panel 100" includes a base substrate 101 including a display area DA and a non-display area NDA. The display area DA of the base substrate 101 may include (or be coincident with) a light emitting area LEA-PS for the photo sensor array and a photo sensor array area PSAA'. The non-display area NDA of the base substrate 101 may be disposed outside the display area DA. The photo sensor array includes a plurality of photo sensors PS" arranged in the display area DA between adjacent pixels PXL'. The window 200 includes a fingerprint contact area FCA with which a finger 10 of a user comes in contact. The adhesive layer 400' may couple the window 200 with the display panel 100", and, as such, may be disposed between an encapsulation layer 190 of the display panel 100" and the window 200.

A thin film transistor TFT, an organic light emitting element OLED connected to the thin film transistor TFT, and an encapsulation layer 190 covering the organic light emitting element OLED may be provided in the light emitting area LEA-PS for the photo sensor array of the base substrate 101. The encapsulation layer 190 covers the photo sensor array, which may be disposed between a buffer layer 110 of the display panel 100" and a pixel definition layer 165 of the display panel 100", such as between the buffer layer 110 and a first protection layer 145" of the display panel 100". The thin film transistor TFT and the organic light emitting element OLED may constitute a display element for the photo sensor PS" among display elements for the photo sensor array. In this manner, the display elements are not only arranged in the display area DA, but also in the light emitting area LEA-PS for the photo sensor array.

The photo sensor array includes a photo sensor PS" and a readout line 360" connected to the photo sensor PS". The photo sensor PS" may include a second active pattern 320', a second gate electrode 330', a second source electrode 340', and a second drain electrode 350". The readout line 360" may be connected to (e.g., extend from) the second drain electrode 350" of the photo sensor PS". The second active pattern 320' of the photo sensor PS" may be disposed in the same layer and formed through the same process as a first active pattern 120 of the display element for the photo sensor PS". A longitudinal dimension of the photo sensor PS" (e.g., a longitudinal dimension of the second active pattern 320') may be at least 4 μm, however, exemplary embodiments are not limited thereto or thereby.

The second gate electrode 330' of the photo sensor PS" may be disposed in the same layer and formed through the same process as a first gate electrode 130 of the display element for the photo sensor PS". In one or more exemplary embodiments, the second gate electrode 330' may be connected to a gate line (not shown) of the pixel PXL' (or another pixel adjacent to the pixel PXL') to select (or activate) the pixel PXL' (or the other pixel adjacent to the pixel PXL') and the photo sensor PS". In some exemplary embodiments, a first portion of a gate signal utilized to select the pixel PXL' and a second portion of the gate signal utilized to select the photo sensor PS" may be multiplexed (e.g., time division multiplexed) on a same gate line. In various exemplary embodiments, a pixel circuit (not shown) of the pixel PXL' may include one or more components (e.g., switch elements, such as transistors) to sequentially select the pixel PXL' and the photo sensor PS" utilizing a gate signal of a gate line connected to the pixel PXL'. It is also contemplated that the second gate electrode 330' may be connected to a standalone scanning line (not shown) utilized to select the photo sensor PS". The standalone scanning line may extend parallel to, for instance, gate lines of the display area DA.

The second source electrode 340', the second drain electrode 350", and the readout line 360" of the photo sensor PS" may be disposed in the same layer and formed through the same process as a first source electrode 140 and a first drain electrode 150 of the display element for the photo sensor PS". In one or more exemplary embodiments, the readout line 360" may be connected to a data line (not shown) of the pixel PXL' such that a data voltage utilized to drive the pixel PXL' (or another pixel adjacent to the pixel PXL') and a read out signal of the photo sensor PS" are multiplexed (e.g., time division multiplexed) onto the data line. In some exemplary embodiments, a pixel circuit (not shown) of the pixel PXL' may include one or more components (e.g., switching elements, such as transistors) to sequentially receive the data voltage via a data line and transmit the read out signal on the data line (or another data line). The read out signal may be utilized to detect three dimensional pattern information. It is also contemplated that the readout line 360" may be connected to a standalone sensing line (not shown) utilized to transmit a read out signal of the photo sensor PS". The standalone sensing line may extend parallel to, for instance, data lines of the display area DA.

Although the readout line 360" is shown as being disposed on an interlayer insulating layer 135 of the display panel 100", the readout line 360" may be disposed on the first protective layer 145" of the display panel 100", and, thereby, between the pixel definition layer 165 and the first protection layer 145". In this manner, the readout line 360" and the second drain electrode 350" may be formed similarly to the readout line 360' and the second drain electrode 350' of the photo sensor PS' of FIG. 10, but may, dissimilarly, be disposed in the display area DA and covered by the pixel definition layer 165.

The first protective layer 145" may be disposed over the photo sensor PS" such that the first protective layer 145" includes an opening that exposes a portion of the first drain electrode 150 of the display element. In an exemplary embodiment including the readout line 360" and the second drain electrode 350" being similar to the readout line 360' and the second drain electrode 350' of the photo sensor PS' of FIG. 10, the protective layer 145" may include openings that respectively expose a portion of the first drain electrode 150 of the display element for the photo sensor PS" and a portion of the second drain electrode 350". The first drain electrode 150 is electrically connected to the organic light emitting element OLED through one of the openings of the protective layer 145", and the second drain electrode 350" is electrically connected to the readout line 360" through another one of the openings of the protective layer 145".

The photo sensor PS" senses fingerprint information of the finger 10 of the user using light that is emitted from the organic light emitting element OLED and is then reflected by the finger 10 of the user to be incident with the photo sensor PS". Although FIG. 16 illustrates the organic light emitting element OLED providing the light to sense the fingerprint information, exemplary embodiments are not limited thereto or thereby. For instance, another pixel disposed in the display area DA may additionally or alternatively provide the light.

According to one or more exemplary embodiments, at least one photo sensor PS" may be disposed between adjacent pixels PXL'. Although four photo sensors PS" are shown as being disposed about each pixel PXL', exemplary embodiments are not limited thereto or thereby. For instance, each pixel PXL' may be associated with one photo sensor PS", two photo sensors PS", three photo sensors PS", etc. It is also contemplated that one or more pixels PXL' may not be associated with at least one photo sensor PS". In this manner, any suitable number of photo sensors PS" may be arranged between adjacent pixels PXL'.

Figure 17:
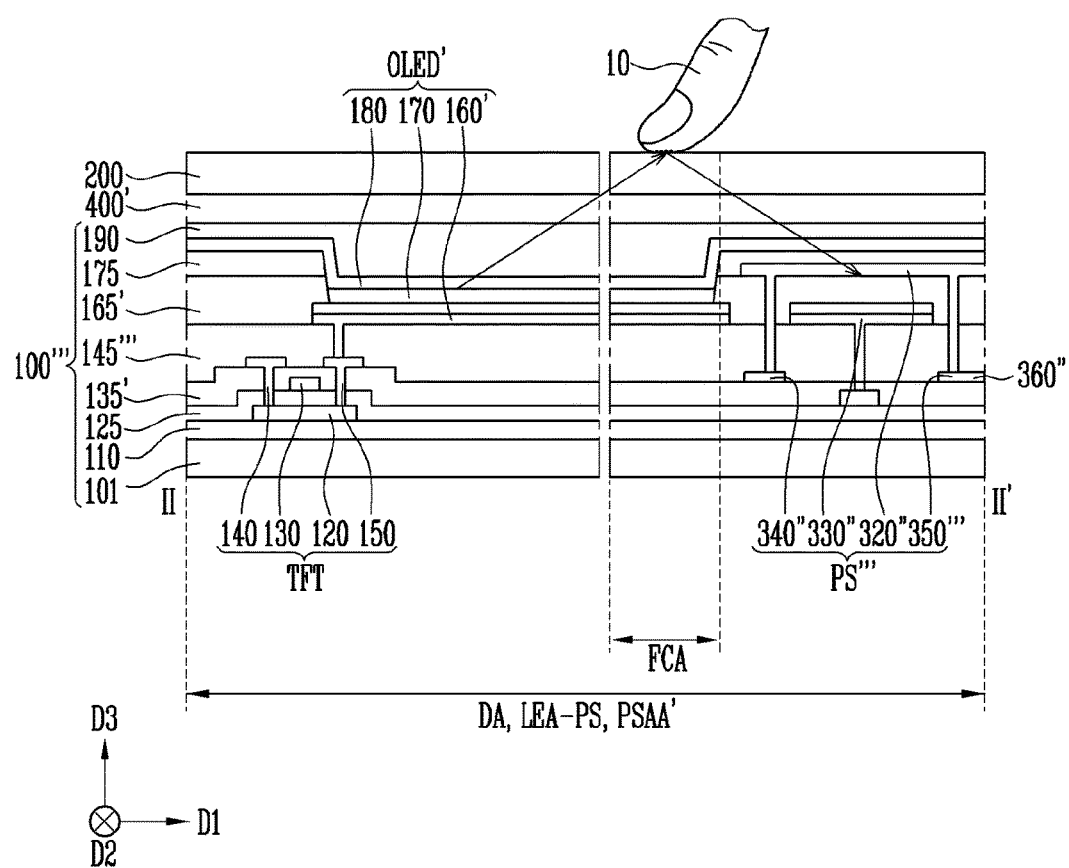
FIG. 17 is a cross-sectional view of a display device taken along sectional line II-II' of FIG. 15, according to one or more exemplary embodiments.

FIG. 17 is a cross-sectional view of a display device taken along sectional line II-II' of FIG. 15, according to one or more exemplary embodiments. The display panel 100'''

(and, thereby, the display device) of FIG. 17 may be similar to the display panels and display devices of FIGS. 9, 10, 15, and 16, and, as such, differences from the display panels and display devices of FIGS. 9, 10, 15, and 16 will mainly be described to avoid redundancy. Portions not described in association with FIG. 17 may correspond to portions described in association with at least one of FIGS. 9, 10, 15, and 16. Identical reference numerals designate identical components, and similar reference numerals designate similar components.

Referring to FIG. 17, the display device includes a display panel 100''', a window 200 disposed on a surface (e.g., upper surface) of the display panel 100''', and a photo sensor array. The display panel 100''' includes a base substrate 101 including a display area DA and a non-display area NDA. The display area DA of the base substrate 101 may include (or be coincident with) a light emitting area LEA-PS for the photo sensor array and a photo sensor array area PSAA'. The non-display area NDA of the base substrate 101 may be disposed outside the display area DA. The photo sensor array includes a plurality of photo sensors PS''' arranged in the display area DA between adjacent pixels PXL'. The window 200 includes a fingerprint contact area FCA with which a finger 10 of a user comes in contact. The adhesive layer 400' may couple the window 200 with the display panel 100''', and, as such, may be disposed between an encapsulation layer 190 of the display panel 100''' and the window 200.

A thin film transistor TFT, an organic light emitting element OLED' connected to the thin film transistor TFT, and an encapsulation layer 190 covering the organic light emitting element OLED' may be provided in the light emitting area LEA-PS for the photo sensor array of the base substrate 101. The encapsulation layer 190 covers the photo sensor array, which may be disposed between a gate insulating layer 125 of the display panel 100''' and the encapsulation layer 190, e.g., between the gate insulating layer 125 and a second electrode 180 of the organic light emitting element OLED'. The thin film transistor TFT and the organic light emitting element OLED' may constitute a display element for the photo sensor PS''' among display elements for the photo sensor array. In this manner, the display elements are not only arranged in the display area DA, but also in the light emitting area LEA-PS for the photo sensor array.

Although the organic light emitting element OLED of FIG. 9 was described as including a first electrode 160 that may be formed as a multilayer structure including a reflective layer and a transparent conductive layer, the organic light emitting element OLED' of FIG. 17 is illustrated as including a first electrode 160' having such a multilayer structure. Exemplary embodiments, however, are not limited thereto or thereby.

The photo sensor array includes a photo sensor PS''' and a readout line 360'' connected to the photo sensor PS'''. The photo sensor PS''' may include a second active pattern 320'', a second gate electrode 330'', a second source electrode 340'', and a second drain electrode 350'''. The readout line 360'' may be connected to (e.g., extend from) the second drain electrode 350''' of the photo sensor PS'''. A longitudinal dimension of the photo sensor PS'' (e.g., a longitudinal dimension of the second active pattern 320'') may be at least 4 μm, however, exemplary embodiments are not limited thereto or thereby.

The second active pattern 320'' of the photo sensor PS''' may be disposed on a pixel definition layer 165' of the display panel 100'''. In one or more exemplary embodiments, the second active pattern 320'' may be formed after the pixel definition layer 165', and may be formed before the organic layer 170 is formed on the first electrode 160'; however, exemplary embodiments are not limited thereto or thereby. To this end, an insulating layer 175 may be formed on the second active pattern 320'' and the pixel definition layer 165' to, for instance, protect the second active pattern 320'' and to insulate the second active pattern 320'' from the second electrode 180. The second active pattern 320'' may be similarly configured as the first active pattern 120 of the display element for the photo sensor PS'''.

A first portion of the second gate electrode 330'' of the photo sensor PS''' may be disposed in the same layer and formed through the same process as a first gate electrode 130 of the display element for the photo sensor PS'''. A second portion of the second gate electrode 330'' of the photo sensor PS''' may be disposed in the same layer and formed through the same process as a first electrode 160' of the organic light emitting element OLED' of the display element for the photo sensor PS'''. To this end, the second portion of the second gate electrode 300'' may have a same layer structure (e.g., multilayer structure) as the first electrode 160'; however, exemplary embodiments are not limited thereto or thereby. For instance, the second gate electrode 320'' may be a single layer structure, whereas the first electrode 160' may be a multilayer structure. Although not illustrated, one or more jumping wires (or pads) may be disposed between the first protective layer 145''' and the interlayer insulating layer 135' to facilitate connection between respective portions of the second gate electrode 330''.

In one or more exemplary embodiments, the second gate electrode 330'' may be connected to a gate line (not shown) of the pixel PXL' (or another pixel adjacent to the pixel PXL') to select (or activate) the pixel PXL' (or the other pixel adjacent to the pixel PXL') and the photo sensor PS'''. In some exemplary embodiments, a first portion of a gate signal utilized to select the pixel PXL' and a second portion of the gate signal utilized to select the photo sensor PS''' may be multiplexed on a same gate line. In some exemplary embodiments, a pixel circuit (not shown) of the pixel PXL' may include one or more components (e.g., transistors) to sequentially select the pixel PXL' and the photo sensor PS''' utilizing a gate signal of a gate line connected to the pixel PXL'. It is also contemplated that the second gate electrode 330'' may be connected to a standalone scanning line (not shown) utilized to select the photo sensor PS'''. The standalone scanning line may extend parallel to, for instance, gate lines of the display area DA.

A first portion of the second source electrode 340'', a first portion of the second drain electrode 350''', and the readout line 360'' of the photo sensor PS''' may be disposed in the same layer and formed through the same process as a first source electrode 140 and a first drain electrode 150 of the display element for the photo sensor PS'''. Second portions of the second source electrode 340'' and the second drain electrode 350''' extend through respective contact holes formed in the pixel definition layer 165' and the first protection layer 145'''. Although not illustrated, one or more jumping wires may be disposed between the pixel definition layer 165' and the first protection layer 145''' to facilitate connection between respective portions of the second active pattern 320'' and the first portions of the second source electrode 340'' and the second drain electrode 350'''.

In one or more exemplary embodiments, the readout line 360'' may be connected to a data line (not shown) of the pixel PXL' such that a data voltage utilized to drive the pixel PXL' (or another pixel adjacent to the pixel PXL') and a read out signal of the photo sensor PS''' are multiplexed (e.g., time division multiplexed) onto the data line. In some exemplary embodiments, a pixel circuit (not shown) of the pixel PXL' may include one or more components (e.g., switching elements, such as transistors) to sequentially receive the data voltage via a data line and transmit the read out signal on the data line (or another data line). It is also contemplated that the readout line 360" may be connected to a standalone sensing line (not shown) utilized to transmit a read out signal of the photo sensor PS'''. The standalone sensing line may extend parallel to, for instance, data lines of the display area DA.

Although the readout line 360" is shown as being disposed on an interlayer insulating layer 135' of the display panel 100''', the readout line 360" may be disposed on the first protective layer 145''', and, thereby, between the pixel definition layer 165' and the first protection layer 145'''. In this manner, the readout line 360" may be formed similarly to the readout line 360' of the photo sensor PS' of FIG. 10, but may, dissimilarly, be disposed in the display area DA and covered by the pixel definition layer 165'.

The first protective layer 145''' may be disposed over the first portions of the second gate electrode 330", the second source electrode 340", and the second drain electrode 350'''. The pixel definition layer 165' may be disposed over the second portion of the gate electrode 330", as well as over the first portions of the second gate electrode 330", the second source electrode 340", and the second drain electrode 350". The second active layer 320" may be disposed on the pixel definition layer 165', such that the second portions of the second source electrode 340" and the second drain electrode 350''' extend through the pixel definition layer 165' and the first protective layer 145'''.

The photo sensor PS''' senses fingerprint information of the finger 10 of the user using light that is emitted from the organic light emitting element OLED' and is then reflected by the finger 10 of the user to be incident with the photo sensor PS'''. Although FIG. 17 illustrates the organic light emitting element OLED' providing the light to sense the fingerprint information, exemplary embodiments are not limited thereto or thereby. For instance, another pixel disposed in the display area DA may additionally or alternatively provide the light.

FIG. 18 is a cross-sectional view of a display device, according to one or more exemplary embodiments. The display panel 100'''' (and, thereby, the display device) of FIG. 18 may be similar to the display panels and display devices of FIGS. 9, 10, and 15-17, and, as such, differences from the display panels and display devices of FIGS. 9, 10, and 15-17 will mainly be described to avoid redundancy. Portions not described in association with FIG. 18 may correspond to portions described in association with at least one of FIGS. 9, 10, and 15-17. To this end, identical reference numerals designate identical components, and similar reference numerals designate similar components.

Referring to FIG. 18, the photo sensor PS'''' may be formed as a photodiode including a photoelectric conversion layer (e.g., a photosensitive layer) 1801, a first electrode 1802, and a second electrode 1803. The first electrode 1802 may function as an anode and the second electrode 1803 may function as a cathode, however, exemplary embodiments are not limited thereto or thereby. To this end, the pixel definition layer 165" may serve as a buffer layer between the photoelectric conversion layer 1801 and the first electrode 1802. An insulating layer 175 may be formed on (e.g., at least partially cover) the photoelectric conversion layer 1801 and the pixel definition layer 165" to, for instance, protect the photoelectric conversion layer 1801 and to insulate the photoelectric conversion layer 1801 from the second electrode 180. In one or more exemplary embodiments, the insulating layer 175 may also be formed on the second electrode 1803.

The photoelectric conversion layer 1801 may generate photoelectrons in response to incident light, e.g., light emitted from organic light emitting element OLED' and reflected off of a finger 10. According to some exemplary embodiments, the photoelectric conversion layer 1801 may be an intrinsic layer that includes both at least one P-type semiconductor and at least one N-type semiconductor. The photoelectric conversion layer 1801 may be formed on the pixel definition layer 165" via, for example, co-deposition; however, exemplary embodiments are not limited thereto or thereby. The photoelectric conversion layer 1801 may further include, in addition to an intrinsic layer, at least one of a P-type layer (not shown) disposed between the intrinsic layer and the first electrode 1802 and at least one of an N-type layer (not illustrated) disposed between the intrinsic layer and the second electrode 1803. The P-type layer may include a P-type semiconductor, but substantially not an N-type semiconductor. The N-type layer may include an N-type semiconductor, but substantially not a P-type semiconductor. It is noted that composition ratios of the P-type semiconductor and the N-type semiconductor may vary depending on their respective positions and sizes in the photoelectric conversion layer 1801. To this end, a longitudinal dimension of the photo sensor PS'''' (e.g., a longitudinal dimension of the photoelectric conversion layer 1801) may be at least 4 µm, however, exemplary embodiments are not limited thereto or thereby.

A first portion of the first electrode 1802 may be disposed in the same layer and formed through the same process as the first gate electrode 130 of the display element for the photo sensor PS''''. A second portion of the first electrode 1802 may be disposed in the same layer and formed through the same process as a first electrode 160' of the organic light emitting element OLED' of the display element for the photo sensor PS''''. To this end, the second portion of the first electrode 1802 may have a same layer structure (e.g., multilayer structure) as the first electrode 160'; however, exemplary embodiments are not limited thereto or thereby. For instance, the first electrode 1802 may be a single layer structure, whereas the first electrode 160' may be a multi-layer structure. Respective portions of the first electrode 1802 may be connected to one another via a contact hole in the first protective layer 145'''' and the interlayer insulating layer 135'. Although not illustrated, one or more jumping wires may be disposed between the first protective layer 145'''' and the interlayer insulating layer 135' to facilitate connection between the respective portions of the first electrode 1802.

According to some exemplary embodiments, the first electrode 1802 may be connected to a gate line (not shown) of the pixel PXL' (or another pixel adjacent to the pixel PXL') to select (or activate) the pixel PXL' (or the other pixel adjacent to the pixel PXL') and the photo sensor PS''''. In some exemplary embodiments, a first portion of a gate signal utilized to select the pixel PXL' and a second portion of the gate signal utilized to select the photo sensor PS'''' may be multiplexed (e.g., time division multiplexed) on a same gate line. In one or more exemplary embodiments, a pixel circuit (not shown) of the pixel PXL' may include one or more components (e.g., switching elements, such as transistors) to sequentially select the pixel PXL' and the photo sensor PS'''' utilizing a gate signal of a gate line connected to the pixel PXL'. It is also contemplated that the first electrode 1802 may be connected to a standalone scanning line (not shown) utilized to select the photo sensor PS''''. The standalone scanning line may extend parallel to, for instance, gate lines of the display area DA.

A first portion of the second electrode 1803 and a readout line 360'' of the photo sensor PS'' may be disposed in the same layer and formed through the same process as the first source electrode 140 and the first drain electrode 150 of the display element for the photo sensor PS''''. A second portion of the second electrode 1803 extends through a contact hole formed in the pixel definition layer 165'' and the first protection layer 145''''. Although not illustrated, one or more jumping wires may be disposed between the pixel definition layer 165'' and the first protection layer 145'''' to facilitate connection between respective portions of the second electrode 1803. It is also contemplated that, in some exemplary embodiments, the second portion of the second electrode 1803 and the readout line 360'' may be disposed in the same layer and formed through the same process as the first electrode 160'.

Although not illustrated, the second electrode 1803 may be formed in an interior region of the photoelectric conversion layer 1801. For instance, the photoelectric conversion layer 1801 may fully or partially surround a portion (not depicted) of the second electrode 1803. Alternatively (or additionally), a portion of the photoelectric conversion layer 1801 may overlap with a portion of the second electrode 1803. For instance, the first portion of the second electrode 1803 may contact a lower portion of the photoelectric conversion layer 1801. A width of the second electrode 1803 in a direction perpendicular to the third direction D3 may be sized such that a portion of the second electrode 1803 overlaps with a portion of the first electrode 1802; however, exemplary embodiments are not limited thereto or thereby. For instance, respective widths and relative distances between the first electrode 1802 and the second electrode 1803 may be sized in any suitable manner.

In one or more exemplary embodiments, the readout line 360'' may be connected to a data line (not shown) of the pixel PXL' such that a data voltage utilized to drive the pixel PXL' (or another pixel adjacent to the pixel PXL') and a read out signal of the photo sensor PS'''' are multiplexed (e.g., time division multiplexed) onto the data line. In some exemplary embodiments, a pixel circuit (not shown) of the pixel PXL' may include one or more components (e.g., switching elements, such as transistors) to sequentially receive the data voltage via a data line and transmit the read out signal on the data line (or another data line). It is also contemplated that the readout line 360'' may be connected to a standalone sensing line (not shown) utilized to transmit a read out signal of the photo sensor PS''''. The standalone sensing line may extend parallel to, for instance, data lines of the display area DA.

According to some exemplary embodiments, the pixel definition layer 165'' may be formed having a single layer or multilayer structure. For instance, the pixel definition layer 165'' may be formed as a single layer of organic material. As another example, the pixel definition layer 165'' may be formed as a multilayer structure including at least one organic layer and at least one inorganic layer. Each of the organic and inorganic layers of the pixel definition layer 165'' may have a thickness in the third direction D3 of about 1 nm to about 100 nm. A highest occupied molecular orbital (HOMO) energy level of the inorganic layer may be between HOMO energy levels of the organic layer and the photoelectric conversion layer 1801. Such a configuration may improve external quantum efficiency of the photo sensor PS''''. It is also noted that the inorganic layer may have a relatively high thermal stability as compared with the organic layer. This may improve reliability of the photo sensor PS''''.

According to one or more exemplary embodiments, the photo sensor PS'''' senses three dimensional pattern information, e.g., fingerprint information of the finger 10 of a user, using light that is emitted from the organic light emitting element OLED' and is then reflected by the finger 10 of the user to be incident with the photo sensor PS''''. Although FIG. 18 illustrates the organic light emitting element OLED' providing the light to sense the fingerprint information, exemplary embodiments are not limited thereto or thereby. For instance, another pixel disposed in the display area DA may additionally or alternatively provide the light. It is also contemplated that the second electrode 180 of the organic light emitting element OLED' may include one or more openings overlapping the photoelectric conversion layer 1801. The presence of the openings may increase the amount of light incident on the photoelectric conversion layer 1801, and, thereby, increase the ability of the photo sensor PS'''' to detect an aspect of a three dimensional pattern, such as an aspect of a fingerprint of the finger 10.

FIG. 19 is a cross-sectional view of a display device taken along sectional line II-II' of FIG. 15, according to one or more exemplary embodiments. The display panel 100'''' (and, thereby, the display device) of FIG. 19 may be similar to the display panels and display devices of FIGS. 9, 10, and 15-18, and, as such, differences from the display panels and display devices of FIGS. 9, 10, and 15-18 will mainly be described to avoid redundancy. Portions not described in association with FIG. 19 may correspond to portions described in association with at least one of FIGS. 9, 10, and 15-18. To this end, identical reference numerals designate identical components, and similar reference numerals designate similar components.

Referring to FIG. 19, the photo sensor PS'''' may be formed as a photodiode including a photoelectric conversion layer (e.g., a photosensitive layer) 1901, a first electrode 1902, and a second electrode 1903. The first electrode 1902 may function as an anode and the second electrode 1903 may function as a cathode, however, exemplary embodiments are not limited thereto or thereby. To this end, the pixel definition layer 165''' may serve as a buffer layer between the photoelectric conversion layer 1901 and the first electrode 1902. An insulating layer 175' may be formed on (e.g., at least partially cover) the photoelectric conversion layer 1801 and the pixel definition layer 165'''. In this manner, the insulating layer 175' may serve as a hole blocking (or electron transport layer) between the second electrode 1903 and the photoelectric conversion layer 1901.

The photoelectric conversion layer 1901 may generate photoelectrons in response to incident light, e.g., light emitted from organic light emitting element OLED'' and reflected off of a finger 10. According to some exemplary embodiments, the photoelectric conversion layer 1901 may be an intrinsic layer that includes both at least one P-type semiconductor and at least one N-type semiconductor. The photoelectric conversion layer 1901 may be formed on the pixel definition layer 165''' via, for example, co-deposition; however, exemplary embodiments are not limited thereto or thereby. The photoelectric conversion layer 1901 may further include, in addition to an intrinsic layer, at least one of a P-type layer (not shown) disposed between the intrinsic layer and the first electrode 1902 and at least one of an N-type layer (not illustrated) disposed between the intrinsic layer and the second electrode 1903. The P-type layer may include a P-type semiconductor, but substantially not an N-type semiconductor. The N-type layer may include an N-type semiconductor, but substantially not a P-type semiconductor. It is noted that composition ratios of the P-type semiconductor and the N-type semiconductor may vary depending on their respective positions and sizes in the photoelectric conversion layer 1901. To this end, a longitudinal dimension of the photo sensor PS'''' (e.g., a longitudinal dimension of the photoelectric conversion layer 1901) may be at least 4 µm, however, exemplary embodiments are not limited thereto or thereby.

A first portion of the first electrode 1902 may be disposed in the same layer and formed through the same process as the first gate electrode 130 of the display element for the photo sensor PS''''. A second portion of the first electrode 1902 may be disposed in the same layer and formed through the same process as a first electrode 160' of the organic light emitting element OLED'' of the display element for the photo sensor PS''''. To this end, the second portion of the first electrode 1902 may have a same layer structure (e.g., multilayer structure) as the first electrode 160'; however, exemplary embodiments are not limited thereto or thereby. For instance, the first electrode 1902 may be a single layer structure, whereas the first electrode 160' may be a multilayer structure. Respective portions of the first electrode 1902 may be connected to one another via a contact hole in the first protective layer 145'''' and the interlayer insulating layer 135'. Although not illustrated, one or more jumping wires may be disposed between the first protective layer 145'''' and the interlayer insulating layer 135' to facilitate connection between the respective portions of the first electrode 1902.

According to some exemplary embodiments, the first electrode 1902 may be connected to a gate line (not shown) of the pixel PXL' (or another pixel adjacent to the pixel PXL') to select (or activate) the pixel PXL' (or the other pixel adjacent to the pixel PXL') and the photo sensor PS''''. In some exemplary embodiments, a first portion of a gate signal utilized to select the pixel PXL' and a second portion of the gate signal utilized to select the photo sensor PS'''' may be multiplexed (e.g., time division multiplexed) on a same gate line. In one or more exemplary embodiments, a pixel circuit (not shown) of the pixel PXL' may include one or more components (e.g., switching elements, such as transistors) to sequentially select the pixel PXL' and the photo sensor PS'''' utilizing a gate signal of a gate line connected to the pixel PXL'. It is also contemplated that the first electrode 1902 may be connected to a standalone scanning line (not shown) utilized to select the photo sensor PS''''. The standalone scanning line may extend parallel to, for instance, gate lines of the display area DA.

A first portion of the second electrode 1903 and a readout line 360'' of the photo sensor PS'''' may be disposed in the same layer and formed through the same process as the first source electrode 140 and the first drain electrode 150 of the display element for the photo sensor PS''''. A second portion of the second electrode 1903 extends through a contact hole formed in the insulating layer 175', the pixel definition layer 165''', and the first protection layer 145''''. It is noted that one or more jumping wires (not shown) may be disposed between the insulating layer 175' and the pixel definition layer 165''' and/or between the pixel definition layer 165''' and the first protection layer 145'''' to facilitate connection between respective portions of the second electrode 1903.

A third portion of the second electrode 1903 may be disposed in the same layer and formed through the same process as the second electrode 180' of the organic light emitting element OLED''. In this manner, the second electrode 180' may include one or more openings 1904 separating the second electrode 180' of the organic light emitting element OLED'' from the second electrode 1903 of the photo sensor PS''''. The opening 1904 in the second electrode 180' may also increase the amount of light incident on the photoelectric conversion layer 1901, and, thereby, increase the ability of the photo sensor PS'''' to detect an aspect of a three dimensional pattern, such as an aspect of a fingerprint of the finger 10. In some exemplary embodiments, the second electrode 180' of the organic light emitting element OLED'' may surround the second electrode 1903 of the photo sensor PS''''. It is also contemplated that, in various exemplary embodiments, the first portion of the second electrode 1903 and the readout line 360'' may be disposed in the same layer and formed through the same process as the first electrode 160' of the organic light emitting element OLED''.

According to one or more exemplary embodiments, a width of the second electrode 1903 in a direction perpendicular to the third direction D3 may be sized such that a portion of the second electrode 1903 overlaps with a portion of the first electrode 1902 with the photoelectric conversion layer 1901 disposed therebetween; however, exemplary embodiments are not limited thereto or thereby. For instance, respective widths and relative distances between the first electrode 1902 and the second electrode 1903 may be sized in any suitable manner.

In one or more exemplary embodiments, the readout line 360'' may be connected to a data line (not shown) of the pixel PXL' such that a data voltage utilized to drive the pixel PXL' (or another pixel adjacent to the pixel PXL') and a read out signal of the photo sensor PS'''' are multiplexed (e.g., time division multiplexed) onto the data line. In some exemplary embodiments, a pixel circuit (not shown) of the pixel PXL' may include one or more components (e.g., switching elements, such as transistors) to sequentially receive the data voltage via a data line and transmit the read out signal on the data line (or another data line). It is also contemplated that the readout line 360'' may be connected to a standalone sensing line (not shown) utilized to transmit a read out signal of the photo sensor PS''''. The standalone sensing line may extend parallel to, for instance, data lines of the display area DA.

According to some exemplary embodiments, the pixel definition layer 165''' may be formed having a single layer or multilayer structure. For instance, the pixel definition layer 165''' may be formed as a single layer of organic material. As another example, the pixel definition layer 165''' may be formed as a multilayer structure including at least one organic layer and at least one inorganic layer. Each of the organic and inorganic layers of the pixel definition layer 165''' may have a thickness in the third direction D3 of about 1 nm to about 100 nm. A highest occupied molecular orbital (HOMO) energy level of the inorganic layer may be between HOMO energy levels of the organic layer and the photoelectric conversion layer 1901. Such a configuration may improve external quantum efficiency of the photo sensor PS''''. It is also noted that the inorganic layer may have a relatively high thermal stability as compared with the organic layer. This may improve reliability of the photo sensor PS''''.

The insulating layer 175' (that may also be referred to as an electron transport layer) may block holes from moving from the second electrode 1903 to the photoelectric conversion layer 1901, thereby promoting light absorption in the photoelectric conversion layer 1901 to produce more excitons, which may increase sensitivity of the photo sensor PS''''.

According to one or more exemplary embodiments, the photo sensor PS'''' senses three dimensional pattern information, e.g., fingerprint information of the finger 10 of a user, using light that is emitted from the organic light emitting element OLED'' and is then reflected by the finger 10 of the user to be incident with the photo sensor PS''''. Although FIG. 19 illustrates the organic light emitting element OLED'' providing the light to sense the fingerprint information, exemplary embodiments are not limited thereto or thereby. For instance, another pixel disposed in the display area DA may additionally or alternatively provide the light.

According various exemplary embodiments, it is possible to provide a display device that improves fingerprint sensing sensitivity. One or more exemplary embodiments also provide fingerprint detection in a display area of a display device.

Although certain exemplary embodiments and implementations have been described herein, other embodiments and modifications will be apparent from this description. Accordingly, the inventive concepts are not limited to such embodiments, but rather to the broader scope of the presented claims and various obvious modifications and equivalent arrangements.

What is claimed is:

1. A display device comprising:
    a substrate comprising:
        a display area; and
        a bezel area outside the display area, the bezel area forming at least one edge of the substrate;
    pixel regions overlapping the display area;
    a window disposed on the substrate; and
    a photo sensor array overlapping a portion of the bezel area and being stacked between the substrate and the window, the photo sensor array being configured to sense epidermal ridge information of a user via light reflected from a touch input of the user,
    wherein one or more of the pixel regions is configured to illuminate a contact area of the touch input with the light.

2. The display device of claim 1, wherein:
    the photo sensor array is disposed on a first surface of the window;
    the contact area is disposed on a second surface of the window, the second surface opposing the first surface; and
    the contact area overlaps a portion of the display area.

3. The display device of claim 2, wherein the contact area overlaps a portion of the bezel area.

4. The display device of claim 1, wherein:
    a first side of the contact area is adjacent to the photo sensor array; and
    a second side of the contact area overlaps some of the one or more pixel regions, the second side opposing the first side.

5. The display device of claim 4, wherein the first side is spaced apart from the photo sensor array by a determined distance.

6. The display device of claim 1, wherein each of the pixel regions comprises:
    a thin film transistor disposed on the substrate; and
    an organic light emitting layer electrically connected to the thin film transistor.

7. The display device of claim 1, wherein the photo sensor array comprises a photo sensitive transistor configured to detect the light reflected from the touch input.

8. The display device of claim 7, wherein:
    the pixel regions are spaced apart from one another along a first direction; and
    the photo sensor array longitudinally extends along a second direction crossing the first direction.

9. The display device of claim 6, further comprising:
    an encapsulation layer overlapping the pixel regions and the photo sensor array, the organic light emitting layer being sealed between the encapsulation layer and the substrate,
    wherein a thickness of the encapsulation layer overlapping the organic light emitting layer is different from a thickness of the encapsulation layer overlapping the photo sensor array.

10. The display device of claim 9, wherein the encapsulation layer is stacked between the photo sensor array and the substrate.

11. The display device of claim 9, wherein the photo sensor array is sealed between the encapsulation layer and the substrate.

12. The display device of claim 1, further comprising:
    pixel electrodes disposed on the substrate, each of the pixel regions comprising a pixel electrode among the pixel electrodes; and
    a sensor readout line disposed on the substrate and being electrically connected to the photo sensor array,
    wherein the sensor readout line is in a same layer as the pixel electrodes or in a layer closer to the window than a layer in which the pixel electrodes are disposed.

* * * * *